United States Patent
Cho

(10) Patent No.: US 10,257,458 B2
(45) Date of Patent: Apr. 9, 2019

(54) RAMP SIGNAL GENERATOR OF IMAGE SENSOR, AND IMAGE SENSOR INCLUDING SAME

(71) Applicant: SAMSUNG ELECTRONICS CO., LTD., Suwon-si (KR)

(72) Inventor: Kyu-Ik Cho, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/868,588

(22) Filed: Jan. 11, 2018

(65) Prior Publication Data

US 2018/0359443 A1 Dec. 13, 2018

(30) Foreign Application Priority Data

Jun. 8, 2017 (KR) .......................... 10-2017-0071392

(51) Int. Cl.
| | |
|---|---|
| *H04N 5/378* | (2011.01) |
| *H04N 5/376* | (2011.01) |
| *H04N 5/374* | (2011.01) |
| *H01L 27/146* | (2006.01) |

(52) U.S. Cl.
CPC ......... *H04N 5/378* (2013.01); *H01L 27/1464* (2013.01); *H04N 5/374* (2013.01); *H04N 5/3765* (2013.01)

(58) Field of Classification Search
CPC .. H04N 5/378; H04N 5/37455; H04N 5/3658; H04N 5/3765; H04N 5/374; H01L 27/1464

USPC ................ 348/216.1, 229.1, 308; 250/208.1; 341/155, 157, 170
See application file for complete search history.

(56) References Cited

U.S. PATENT DOCUMENTS

| | | | |
|---|---|---|---|
| 6,885,331 B2 | 4/2005 | Krymski | |
| 6,927,610 B2 | 8/2005 | Callahan, Jr. | |
| 7,271,632 B2 | 9/2007 | Cottin et al. | |
| 7,804,535 B2 | 9/2010 | Muramatsu et al. | |
| 7,816,955 B2 | 10/2010 | Takahashi et al. | |
| 8,106,801 B2 | 1/2012 | Dasnurkar | |
| 8,742,313 B2 | 6/2014 | Takamiya et al. | |
| 8,841,594 B2 * | 9/2014 | Lee ........................ | H04N 5/378 250/208.1 |
| 9,093,998 B2 | 7/2015 | Kinyua et al. | |
| 9,385,694 B2 | 7/2016 | Larsen et al. | |
| 9,513,161 B2 | 12/2016 | Song et al. | |

(Continued)

*Primary Examiner* — Yogesh K Aggarwal
(74) *Attorney, Agent, or Firm* — Sughrue Mion, PLLC

(57) ABSTRACT

A ramp signal generator is provided. The ramp signal generator includes a bias generation circuit, a transferring switch, a sampling capacitor, a current cell circuit, a current to voltage converter and a tuning circuit. The bias generation circuit generates a bias voltage. The transferring switch transfers the bias voltage to a sampling node in response to a first switching control signal. The sampling capacitor samples the bias voltage. The current cell circuit provides a first output node with a first ramping current in response to a sampled bias voltage and switching code pairs. The current to voltage converter includes a first load resistor to convert the first ramping current to a first ramp signal. The tuning circuit includes a capacitor that couples the sampled bias voltage to the first ramp signal, and adjusts a degree of nonlinearity of the first ramp signal in response to a tuning signal.

20 Claims, 18 Drawing Sheets

(56) References Cited

U.S. PATENT DOCUMENTS

2007/0194962 A1* 8/2007 Asayama ............ H03M 1/1014
          341/144
2016/0248409 A1   8/2016 Song
2016/0301883 A1  10/2016 Kim

* cited by examiner

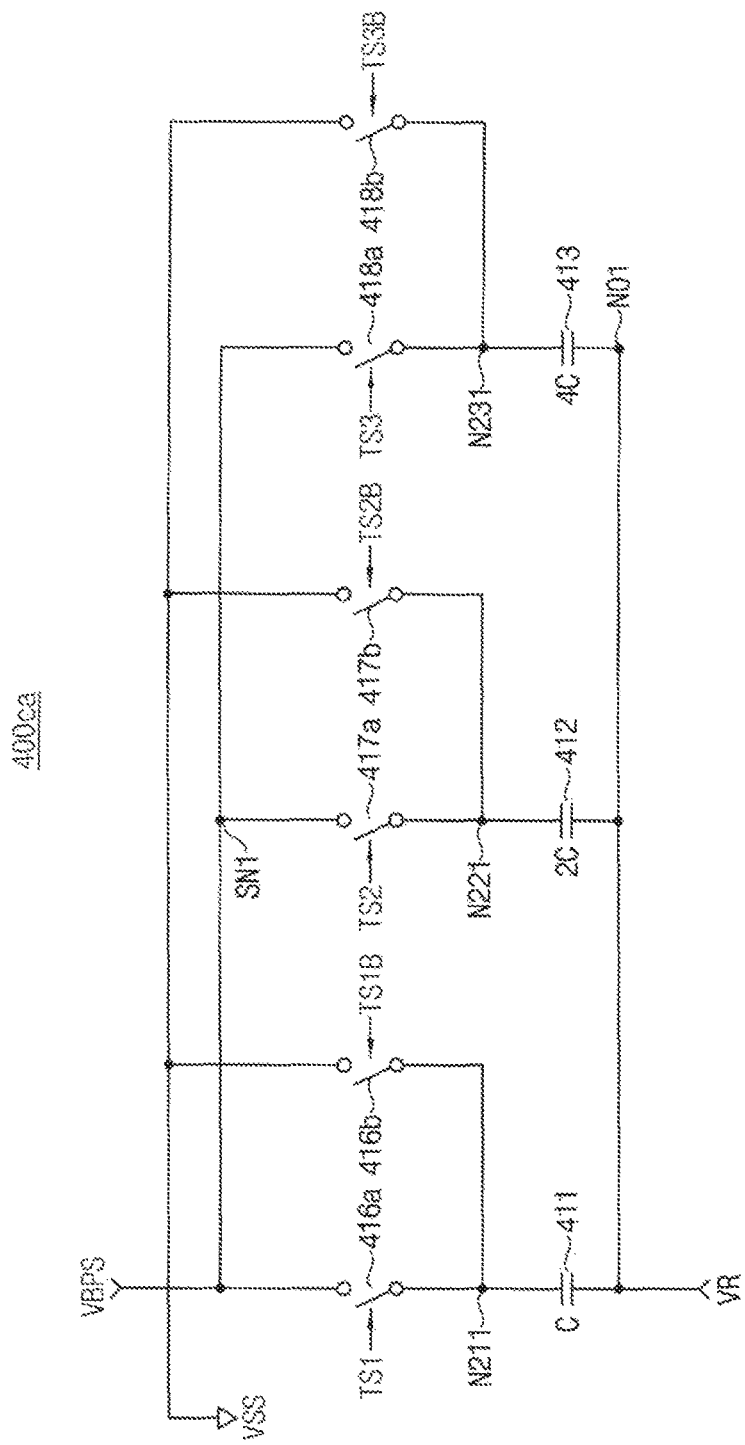

RAMP SIGNAL GENERATOR OF IMAGE SENSOR, AND IMAGE SENSOR INCLUDING SAME

CROSS-REFERENCE TO RELATED APPLICATION

This application claims priority under 35 USC § 119 to Korean Patent Application No. 10-2017-0071392, filed on Jun. 8, 2017 in the Korean Intellectual Property Office (KIPO), the content of which is herein incorporated by reference in its entirety.

BACKGROUND

1. Technical Field

Exemplary embodiments relate to image processing, and more particularly to ramp signal generators of image sensors and image sensors.

2. Discussion of the Related Art

A complementary metal oxide semiconductor (CMOS) image sensor is a solid-state image pickup device manufactured using CMOS processes. The CMOS image sensor has lower manufacturing costs and a smaller size than a charge coupled device (CCD) image sensor which includes a high-voltage analog circuit, and thus, has an advantage of low power consumption. In addition, as the performance of the CMOS image sensor has been improved, this solid-state image pickup device has gained more popularity that the CCD image sensor for various electronic appliances including portable devices such as a smart phone and a digital camera.

A pixel array included in the CMOS image sensor may include a photoelectric conversion element in each pixel. The photoelectric conversion element generates an electrical signal varying with a quantity of incident light. The CMOS image sensor processes electrical signals to produce image data.

The CMOS image sensor generally uses a single-slope analog to digital (AD) conversion method for AD conversion. In the single-slope AD conversion method, a ramp signal monotonously changing in one direction over time is compared with a pixel signal having a predetermined voltage level, and at a time (or a time point) when a voltage level of the ramp signal is equal to a voltage level of the pixel signal, the pixel signal is converted into a digital signal.

Therefore, linearity of the ramp signal affects AD conversion in the image sensors, particularly when the single-slope AD conversion operates at high speed.

SUMMARY

It is an aspect to provide a ramp signal generator of an image sensor, capable of adjusting a degree of nonlinearity of a ramp signal.

It is another aspect to provide an image sensor including the ramp signal generator, capable of adjusting a degree of nonlinearity of a ramp signal.

According to some exemplary embodiments, a ramp signal generator of an image sensor includes a bias generation circuit, a transferring switch, a sampling capacitor, a current cell circuit, a current to voltage converter and a tuning circuit. The bias generation circuit is connected between a first voltage and a second voltage and generates a bias voltage. The transferring switch transfers the bias voltage to a sampling node in response to a first switching control signal. The sampling capacitor is connected between the first voltage and the sampling node, and samples the bias voltage. The current cell circuit provides a first output node with a first ramping current during a ramping period, in response to a sampled bias voltage of the sampling node and a plurality of switching code pairs. The current to voltage converter including at least a first load resistor connected between the first output node and the second voltage, and the first load resistor converts the first ramping current to a first ramp signal which is ramping during the ramping period. The tuning circuit is connected between the first output node and the sampling node, includes at least one capacitor that couples the sampled bias voltage to the first ramp signal, and adjusts a degree of nonlinearity of the first ramp signal in response to a tuning signal.

According to some exemplary embodiments, an image sensor includes a pixel, a comparator, a counter, a ramp signal generator, and a timing controller. The pixel generates a reset signal and an image signal. The comparator compares the reset signal with a first ramp signal to generate a first comparison signal, and compares the image signal with the first ramp signal to generate a second comparison signal. The counter counts the first comparison signal based on a clock signal to generate a first counting value, and counts the second comparison signal based on the clock signal to generate a second counting value. The ramp signal generator generates at least the first ramp signal. The timing controller controls the pixel, the counter and the ramp signal generator. The ramp signal generator includes a tuning circuit connected between a first output node and a sampling node, the first ramp signal is provided at the first output node and a bias voltage is sampled at the sampling node. The tuning circuit adjusts a degree of nonlinearity of the first ramp signal in response to a tuning signal.

According to some exemplary embodiments, a ramp signal generator of an image sensor includes a bias generation circuit, a transferring switch, a sampling capacitor, a current cell, a load resistor and a tuning circuit. The bias generation circuit is connected between a first voltage and a second voltage and generates a bias voltage. The transferring switch transfers the bias voltage to a sampling node in response to a first switching control signal. The sampling capacitor is connected between the first voltage and the sampling node, and samples the bias voltage. The current cell provides a first output node with a cell current during a ramping period, in response to a sampled bias voltage of the sampling node and a switching code pair. The load resistor is connected between the first output node and the second voltage, and the load resistor converts the cell current to a ramp signal. The tuning circuit is connected between the first output node and the sampling node, includes at least one capacitor that couples the sampled bias voltage to the first ramp signal, and adjusts a degree of nonlinearity of the first ramp signal in response to a tuning signal.

BRIEF DESCRIPTION OF THE DRAWINGS

Illustrative, non-limiting exemplary embodiments will be more clearly understood from the following detailed description in conjunction with the accompanying drawings, in which:

FIG. 7B is a circuit diagram illustrating another example of a tuning circuit of the ramp signal generator in FIG. 4A, according to exemplary embodiments;

DETAILED DESCRIPTION OF EXEMPLARY EMBODIMENTS

Various example embodiments will be described more fully with reference to the accompanying drawings, in which embodiments are shown.

Figure 1:
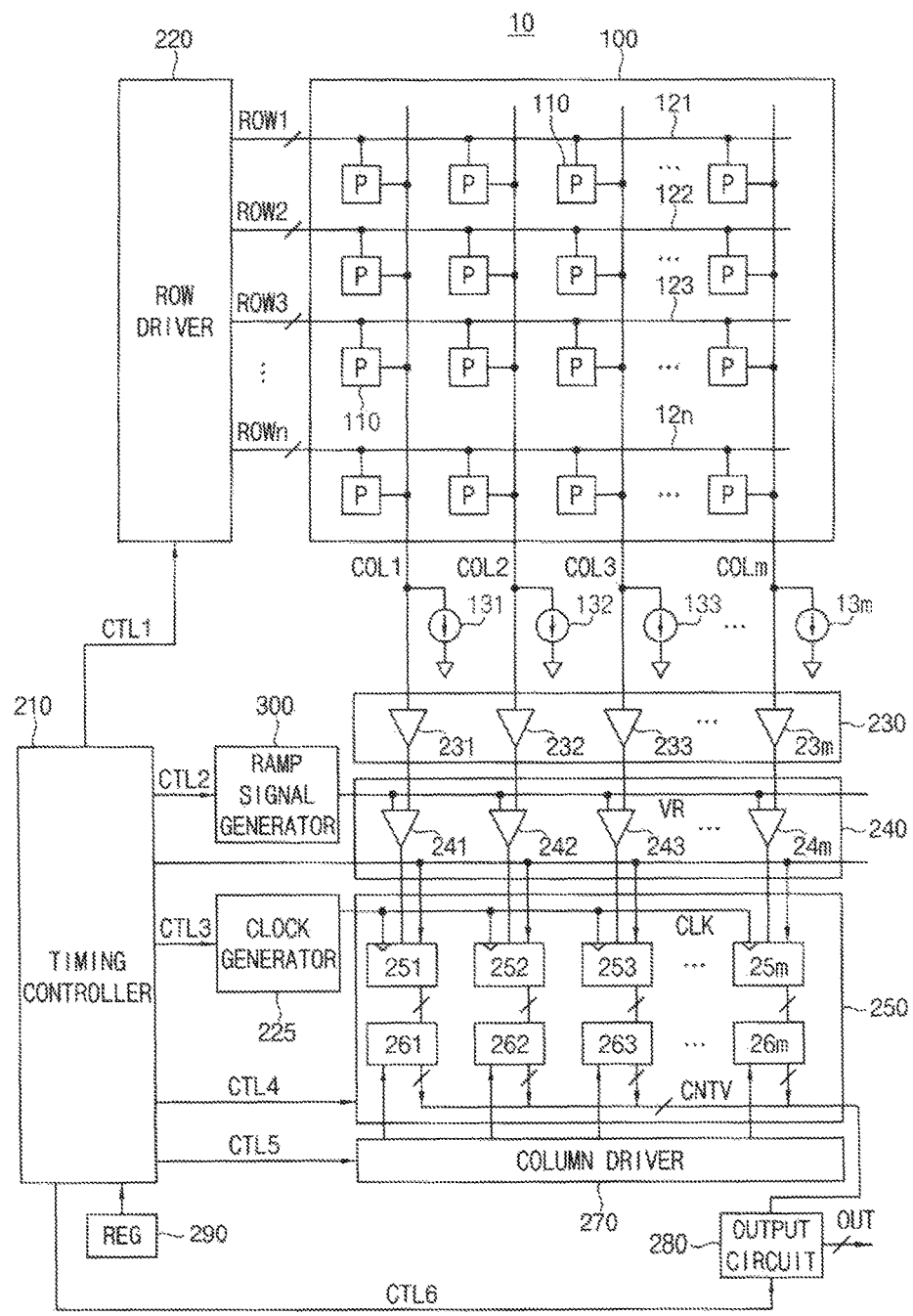
FIG. 1 is a block diagram illustrating an image sensor according to exemplary embodiments.

FIG. 1 is a block diagram illustrating an image sensor according to exemplary embodiments.

Referring to FIG. 1, an image sensor 10 may include a pixel array 100, bias circuits 131, a row driver 220, an amplifier circuit 230, a ramp signal generator 300, a comparator circuit 240, a clock generator 225, a counter circuit 250, a timing controller 210, a column driver 270, and an output circuit 280. An analog to digital (AD) converter circuit may include the comparator circuit 240 and the counter circuit 250.

The image sensor 10 may also include a register 290 that stores control information about the timing controller 210. The register 290 may be implemented as a special function register (SFR), but the inventive concept is not restricted to this example. The image sensor 10 may be a front side illumination (FSI) image sensor or a back side illumination (BSI) image sensor depending on whether a light receiving surface is at the front or back side of a substrate.

The array 100 may be an active pixel sensor (APS) array. The pixel array 100 may include a plurality of pixels 110. The pixels 110 may include a red pixel, a green pixel, and a blue pixel, but the inventive concept is not restricted to the current exemplary embodiment shown in FIG. 1. For example, the pixels 110 may include, alternatively or additionally, a cyan pixel, a yellow pixel, a magenta pixel, or a white pixel.

A red pixel may generate a pixel signal (or charges) corresponding to a red signal in response to wavelengths in the red range of the visible spectrum. A green pixel may generate a pixel signal (or charges) corresponding to a green signal in response to wavelengths in the green range of the visible spectrum. A blue pixel may generate a pixel signal (or charges) corresponding to a blue signal in response to wavelengths in the blue range of the visible spectrum.

Some of the pixels 110 may be controlled to have a relatively long exposure time and the rest of the pixels 110 may be controlled to have a relatively short exposure time. Each of the pixels 110 may include a first photoelectric conversion element controlled with a long exposure time and a second photoelectric conversion element controlled with a short exposure time. In other words, each of the pixels 110 may include at least two photoelectric conversion elements.

Rows ROW1 through ROWn (where "n" is a natural number of at least 4) may respectively include control lines 121, 122, through 12$n$ that control operations of the pixels 111 arranged in the rows ROW1 through ROWn.

The row driver 220 may generate control signals to control operations of the pixels 110 in the rows ROW1 through ROWn according to a control of the timing controller 210.

The bias circuits 131, 132, through 13$m$ may be respectively connected to column lines COL1 through COLm (where "m" is a natural number of at least 4). Each of the bias circuits 131, 132, through 13$m$ may function as a constant current source.

The amplifier circuit 230 may receive and amplify pixel signals output from the column lines COL1 through COLm. The pixels 110 arranged in each of the column lines COL1 through COLm may be connected to a corresponding one of the column lines COL1 through COLm. The amplifier circuit 230 may include amplifiers 231, 232, through 23$m$. Each of the amplifiers 231, 232, through 23$m$ may receive and amplify a pixel signal output from one of the column lines COL1 through COLm.

The ramp signal generator 300 may generate a ramp signal VR that is ramping (monotonously increases or decreases over time) during a ramping period according to a control of the timing controller 210. When the ramp signal generator 300 generates the ramp signal VR that is ramping during the ramping period, the ramp signal generator 300 may increase a linearity of the ramp signal VR by adjusting a degree of nonlinearity that may occur in the ramp signal VR. This will be described in more detail below.

The comparator circuit 240 may convert analog signals amplified by the amplifier circuit 230 into digital signals. The comparator circuit 240 may include comparators 241, 242, through 24m. Each of the comparators 241, 242, through 24m may convert an analog signal output from one of the amplifiers 231, 232, through 23m into a digital signal based on the ramp signal VR.

Each of the comparators 241, 242, through 24m may output a comparison signal that transits from a first level to a second level when a level of the ramp signal VR is equal to a level of an output signal of one of the amplifiers 231, 232, through 23m. A level transition time of the comparison signal may be determined depending on a level of a pixel signal output from one of the pixels 110. The first level may be either a high level or a low level and the second level may be the other.

The clock generator 225 may generate a clock signal CLK applied to the counter circuit 250. Generation timing and frequency of the clock signal CLK may be controlled by the timing controller 210.

The counter circuit 250 may include counters 251, 252, through 25m and memories 261, 262, through 26m. Each of the counters 251, 252, through 25m may count the level transition time of the comparison signal output from one of the comparators 241, 242, through 24m in response to the clock signal CLK and may output a counting value CNTV.

Each of the counters 251, 252, through 25m may be implemented as an up-counter or a down-counter. It is assumed that the counters 251, 252, through 25m are up-counters in the current embodiment shown in FIG. 1. For example, each of the counters 251, 252, through 25m may output the counting value CNTV that sequentially increases unitl the level transition time of the comparison signal and may hold the counting value CNTV at the level transition time.

However, when the counters 251, 252, through 25m are implemented as down-counters, the counters 251, 252, through 25m may operate in the manner opposite to the up-counters.

The counters 251, 252, through 25m may be implemented as L-bit up-counters, where L is a natural number of at least 2. For instance, the counters 251, 252, through 25m may be 10-bit up-counters or 12-bit up-counters but are not restricted thereto.

Each of the memories 261, 262, through 26m may store the counting value CNTV output from one of the counters 251, 252, through 25m. Each of the memories 261, 262, through 26m may be implemented as static random access memory (SRAM), a latch, a flip-flop, or a combination thereof, but the inventive concept is not restricted to the current embodiment shown in FIG. 1. When the counting value CNTV is composed of L bits, each of the memories 261, 262, through 26m may store L bits.

A clock signal (not shown) to control operations of the memories 261, 262, through 26m may be generated by the clock generator 225 or the timing controller 210. The clock signal may be different from the clock signal CLK.

The timing controller 210 may generate control signals to control the operations of the row driver 220, the ramp signal generator 300, the clock generator 225, the counter circuit 250, the column driver 270 and the output circuit 280. The timing controller 210 may control the row driver 220 through a first control signal CTL1, may control the ramp signal generator 300 through a second control signal CTL2, may control the clock generator 225 through a third control signal CTL3, may control the counter circuit 250 through a fourth control signal CTL4, may control the column driver 270 through a fifth control signal CTL5 and may control the output circuit 280 through a sixth control signal CTL6.

The operation of the timing controller 210 may be controlled according to values stored in the register 290. The values stored in the register 290 may be programmed or set by an external device.

The column driver 270 may control an output timing of the counting value CNTV stored in each of the memories 261, 262, through 26m according to the control of the timing controller 210. The memories 261, 262, through 26m may sequentially output the counting value CNTV to the output circuit 280 according to a control of the column driver 270.

The output circuit 280 may receive the counting value CNTV from one of the memories 261 through 26m (that is, sequentially), and may generate a final counting value OUT based on the counting value CNTV corresponding to the reset signal and the counting value CNTV corresponding to the image signal. The output circuit 280 may output the counting value CNTV corresponding to a difference between the reset signal and the image signal from the pixels 110 as the final counting value OUT.

Figure 2:
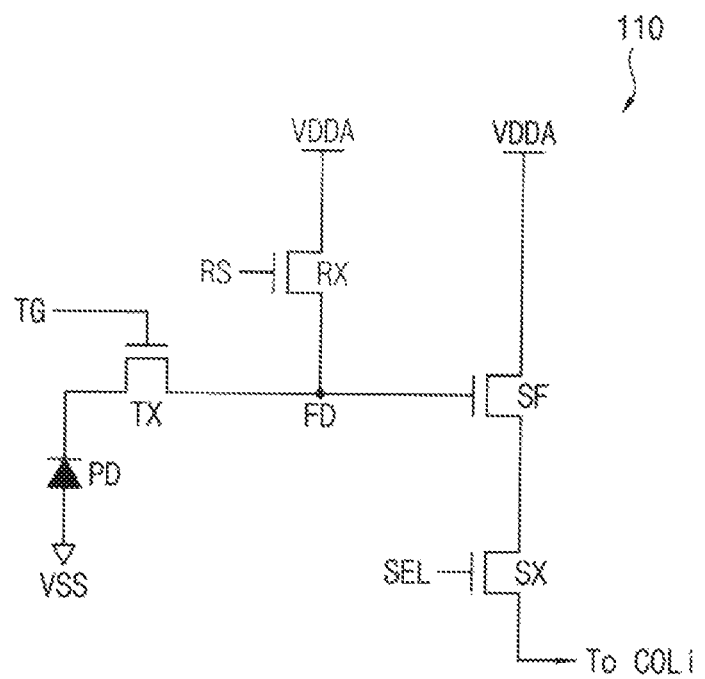
FIG. 2 is a circuit diagram of a pixel illustrated in FIG. 1 according to exemplary embodiments.

FIG. 2 is a circuit diagram of a pixel P illustrated in FIG. 1 according to exemplary embodiments.

Referring to FIGS. 1 and 2, the structure and operations are substantially the same or similar among the pixels 110 illustrated in FIG. 1.

According to an exemplary embodiment, the pixel 110 may include one photoelectric conversion element PD and four transistors TX, RX, SF, and SX. According to other exemplary embodiments, the pixel 110 may include one photoelectric conversion element PD and three or five transistors.

The photoelectric conversion element PD may be implemented as a photodiode, a phototransistor, a photogate, or a pinned photodiode.

The photoelectric conversion element PD may generate charges (e.g., electrons and/or holes) in response to light coming through a filter. The filter may be a red filter, a green filter, or a blue filter but is not restricted thereto. VDDA may denote a power supply voltage and VSS may denote a ground voltage.

The transfer (or, transmission) transistor TX may transfer charges generated by the photoelectric conversion element PD to a floating diffusion region FD in response to a transfer control signal TG. The reset transistor RX may reset the floating diffusion region FD in response to a reset signal RS. The source follower SF may perform source following in response to a voltage corresponding to charges accumulated at the floating diffusion region FD. The selection transistor SX may output a signal output from the source follower SF as a pixel signal to a corresponding column line COLi (where, i=1~m) in response to a selection signal SEL.

Enabling or disabling timings of the control signals TG, RS, and SEL may be controlled by the row driver 220 in turn controlled by the timing controller 210. A enabling transition may be a transition from either a low level to a high level, or from a high level to a low level, and a disabling transition may be a reverse transition to the enabling transition. The control signals TG, RS, and SEL may be transmitted to the pixel 110 through the control lines 121, 122, through 12n arranged in the respective rows ROW1 through ROWn.

Figure 3A:
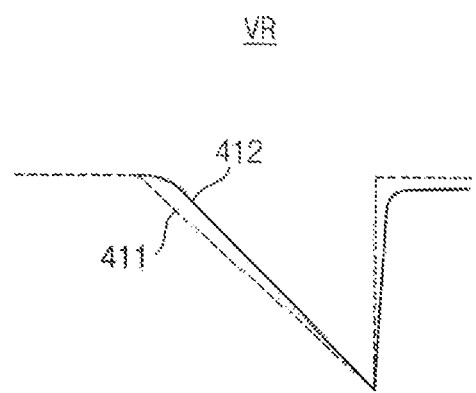
FIGS. 3A and 3B are diagrams for explaining linearity of a ramp signal generated by a ramp signal generator in FIG. 1.
Figure 3B:
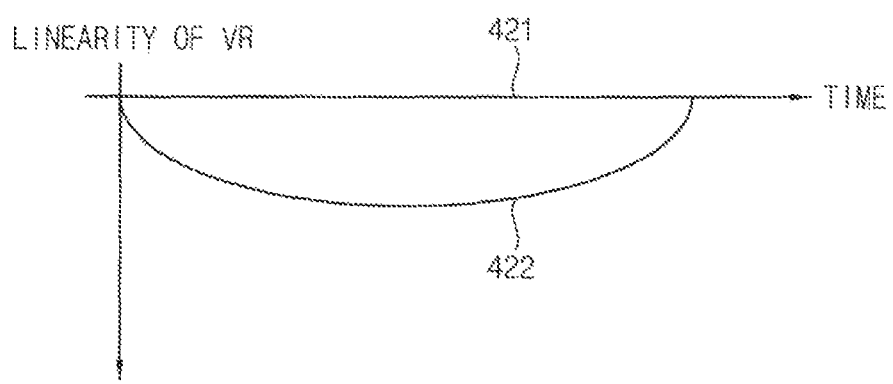

FIGS. 3A and 3B are diagrams for explaining linearity of a ramp signal generated by the ramp signal generator 300 in FIG. 1.

In FIG. 3A, a reference numeral 411 represents an ideal waveform of the ramp signal VR and a reference numeral 412 represents a practical waveform of the ramp signal VR.

In FIG. 3B, a reference numeral 421 represents a linearity of the ramp signal VR when the ramp signal VR has the ideal waveform 411 and a reference numeral 422 represents a linearity of the ramp signal VR when the ramp signal VR the practical waveform 422.

Figure 3C:
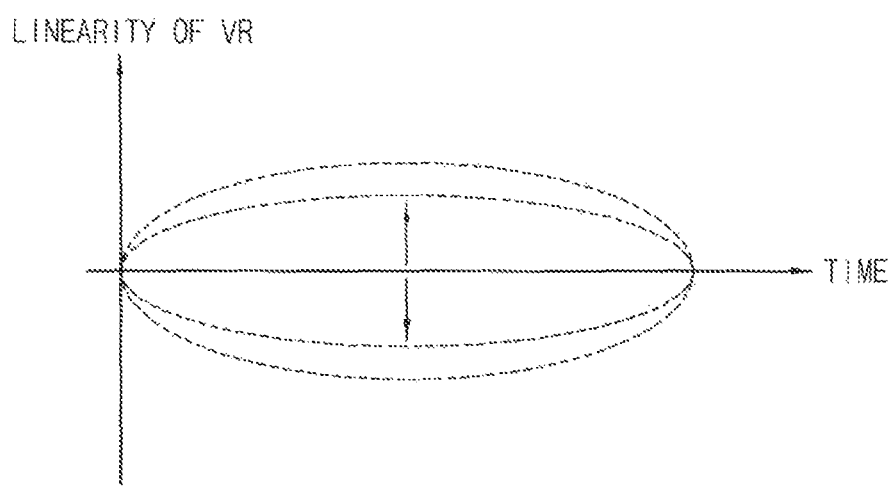
FIG. 3C illustrates that the ramp signal may have nonlinearity due to various reasons.

FIG. 3C illustrates that the ramp signal has the nonlinearity due to various reasons.

As is noted from FIGS. 3B and 3C, the ramp signal VR has nonlinearity in an initial stage of the ramping period. When the ramp signal VR is provided to each of the comparators 241, 242, through 24m of the comparator circuit 240 in FIG. 1 with the nonlinearity of the ramp signal VR not being adjusted, there is increased possibility that errors occur in a counting operation from a low code. The counting operation from a low code may denote performing AD conversion on the reset signal output from the pixel 110 using the ramp signal VR that changes (or ramps) from a level corresponding to a minimum reset counting value of the counter 251 or performing AD conversion on the image signal output from the pixel 110 using the ramp signal VR that changes (or ramps) from a level corresponding to a minimum image signal counting value of the counter 251.

However, the ramp signal generator 300 may reduce the possibility that errors occur in a counting operation from a low code by adjusting a degree of the nonlinearity of the ramp signal VR to increase the linearity of the ramp signal VR. This will be described further below.

Figure 4A:
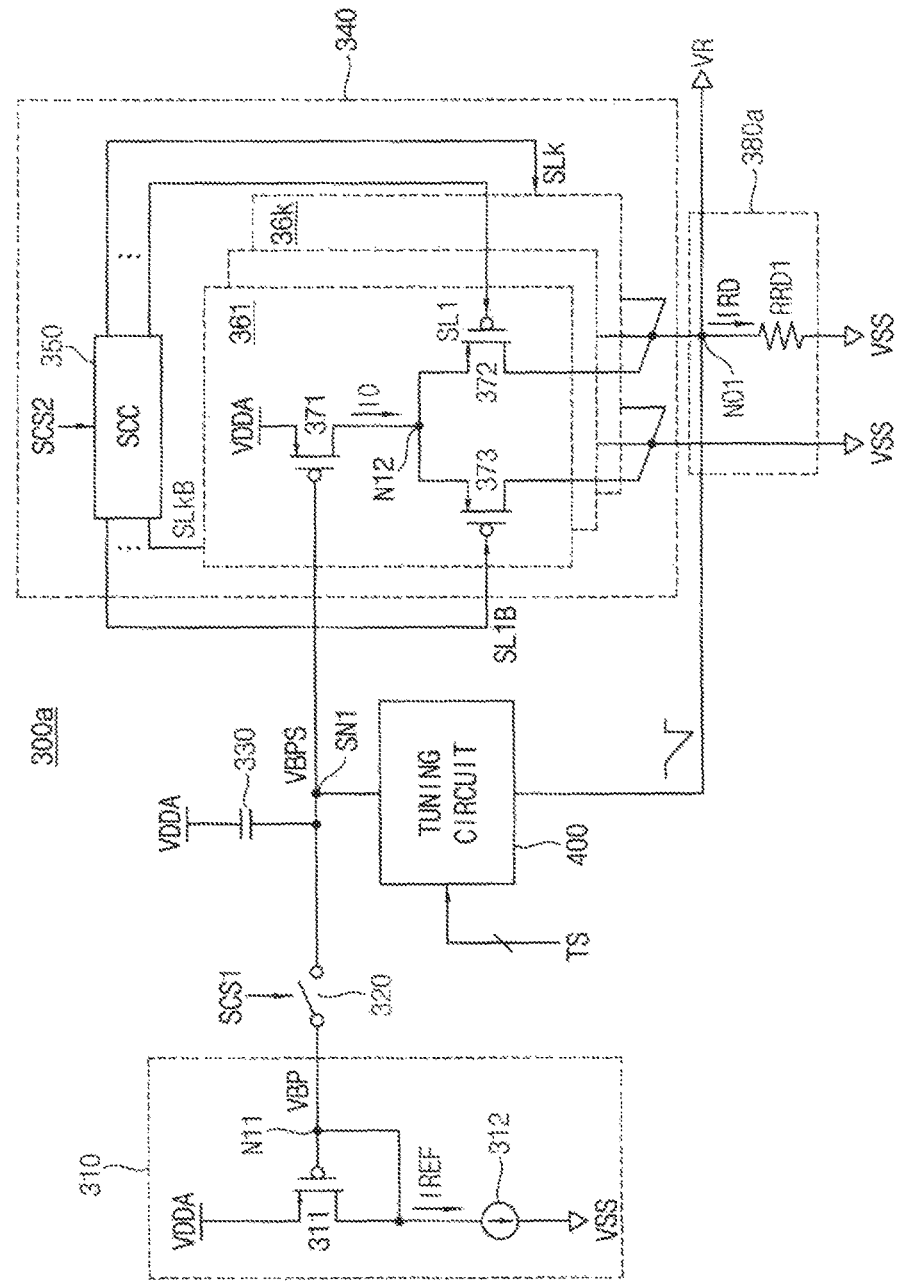
FIG. 4A is a circuit diagram illustrating an example of a ramp signal generator in the image sensor of FIG. 1, according to exemplary embodiments.

FIG. 4A is a circuit diagram illustrating an example of the ramp signal generator in the image sensor of FIG. 1, according to exemplary embodiments.

Referring to FIG. 4A, a ramp signal generator 300a may include a bias generation circuit 310, a transferring switch 320, a sampling capacitor 330, a current cell circuit 340, a current to voltage converter 380a and a tuning circuit 400.

The bias generation circuit 310 is connected between a first voltage (for example, a power supply voltage VDDA in the example shown in FIG. 4A) and a second voltage (for example, a ground voltage VSS in the example shown in FIG. 4A). The bias generation circuit 310 generates a bias voltage VBP. The bias generation circuit 310 includes a p-channel metal-oxide semiconductor (PMOS) transistor 311 and a constant current source 312. The PMOS transistor 311 includes a source connected to the power supply voltage VDDA, a gate connected to a first node N11 and a drain connected to the constant current source 312. Drain of the PMOS transistor 311 is also connected to the first node N11. A reference current IREF flows from the first node N11 to the ground voltage VSS. Therefore, a voltage at the first node N11 corresponds to the bias voltage VBP due to the reference current IREF.

The transferring switch 320 is connected between the first node N11 and a sampling node SN1, and transfers the bias voltage VBP to the sampling node SN1 in response to a switching control signal SCS1.

The sampling capacitor 330 is connected between the power supply voltage VDDA and the sampling node SN1, and samples the bias voltage VBP to provide a sampled bias voltage VBPS.

The current cell circuit 340 may include a switching code controller 350 and a plurality of current cells 361~36k (where, k is a natural number of at least 4).

The switching code controller 350 provides each of a plurality of switching code pairs (SL1, SL1B)~(SLk, SLkB) to corresponding one of the current cells 361~36k, in response to a second switching control signal SCS2. That is, the switching code controller 350 provides a switching code pair (SL1, SL1B) to current cell 361, a switching code pair (SL2, SL2B) to a current cell 362, . . . , and a switching code pair (SLk, SLkB) to current cell 36k. The current cells 361-36k are connected between the sampling node SN1 and a first output node NO1, and each of the current cells 361-36k provides a corresponding cell current IO to the first output node NO1, in response to the sampled bias voltage VBPS and a corresponding one of the switching code pairs (SL1, SL1B)~(SLk, SLkB) The cell currents IO are summed to a ramping current IRD at the first output node NO1.

The first switching control signal SCS 1 and the second switching control signal SCS2 may be included in the first control signal CTL1 in FIG. 1.

Each of the current cells 361~36k includes a first PMOS transistor 371, a second PMOS transistor 372, and a third PMOS transistor 373. The first PMOS transistor 371 has a source connected to the power supply voltage VDDA, a gate connected to the sampling node SN1 and a drain connected to a second node N12. The second PMOS transistor 372 has a source connected to the second node N12, a gate to receive a first switching code SL1 of the switching code pair (SL1, SL1B) and a drain connected to the first output node NO1. The third PMOS transistor 373 has a source connected to the second node N12, a gate to receive a first switching code SL1B of the switching code pair (SL1, SL1B) and a drain connected to the ground voltage VSS. The first through third PMOS transistors 371~373 may be also referred to as first through third transistors, respectively. In this case, the source may be referred to as a first electrode and the drain may be referred to as a second electrode.

The first switching codes SL1~SLk sequentially transit to a high level, the ramping current IRD monotonously decreases and the ramp signal VR down ramps.

The current to voltage converter 380a includes a first load resistor RRD1 connected between the first output node NO1 and the ground voltage VSS and converts the ramping current IRD to a corresponding ramp signal VR.

Since all of the first switching codes SL1~SLk have a low level during an initial stage of the ramping period, the cell current IO may increase due to parasitic capacitance between the second PMOS transistor 372 and the second node N12 during the initial stage of the ramping period. Therefore, the ramp signal VR may have a nonlinear characteristic as described with reference to FIG. 3A.

For adjusting the nonlinear characteristic of the ramp signal VR, the tuning circuit 400 includes at least one capacitor connected between the first output node NO1 and the sampling node SN1, couples the sampled bias voltage VBPS to the ramp signal VR in response to a tuning signal TS and adjusts the sampled bias voltage VBPS. When the sampled bias voltage VBPS is adjusted, the cell current IO changes and the tuning circuit 400 may adjust a degree of nonlinearity of the ramp signal VR by adjusting the sampled bias voltage VBPS. The tuning circuit 400 adjusts a degree of coupling of the sampled bias voltage VBPS to the ramp signal VR in response to the tuning signal TS to artificially generate another nonlinear characteristic to cancel the nonlinear characteristic of the ramp signal VR. Here, "artificially" denotes that the nonlinear characteristic is generated purposefully rather than as a result of a nonlinear aspect of some circuit component.

Figure 4B:
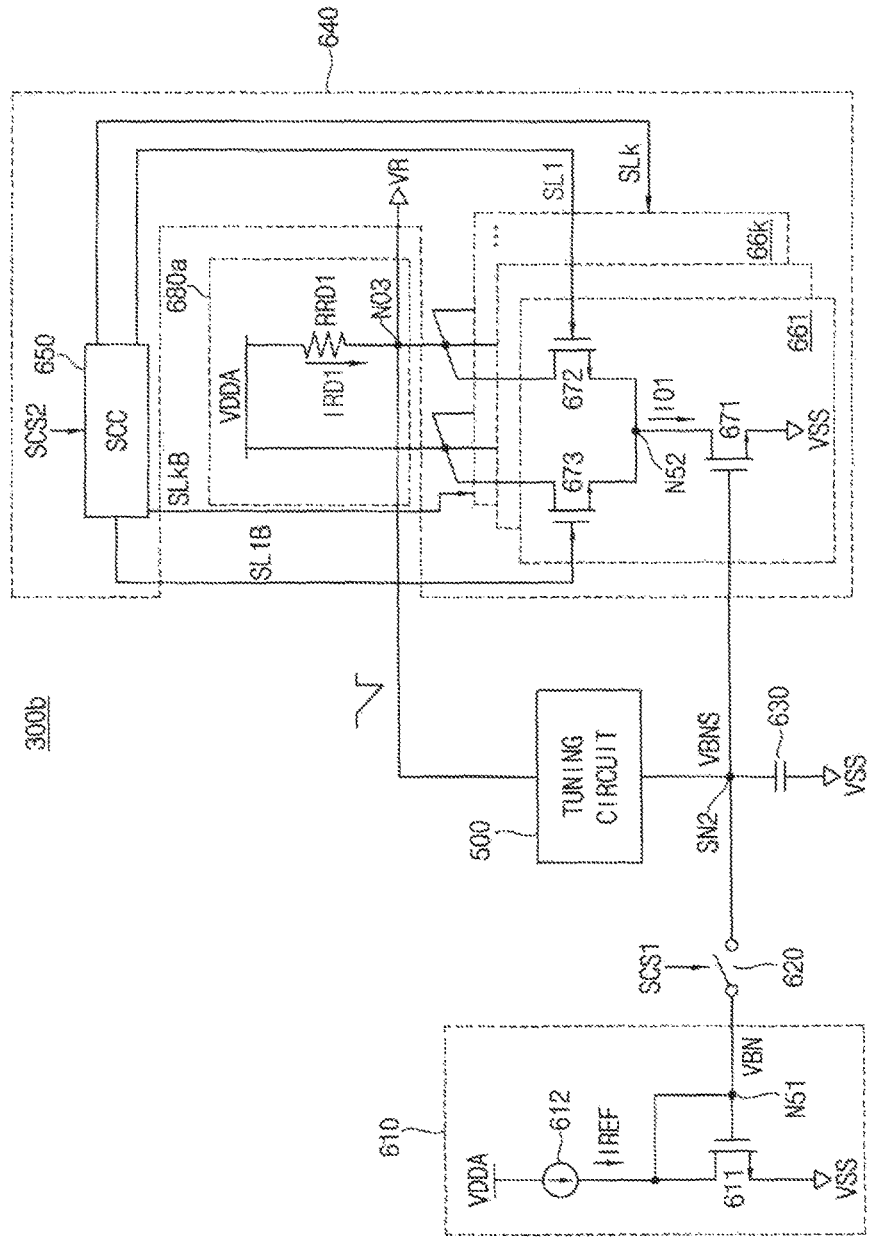
FIG. 4B is a circuit diagram illustrating another example of the ramp signal generator in the image sensor of FIG. 1, according to exemplary embodiments.

FIG. 4B is a circuit diagram illustrating another example of the ramp signal generator in the image sensor of FIG. 1 according to exemplary embodiments.

Referring to FIG. 4B, a ramp signal generator 300b may include a bias generation circuit 610, a transferring switch 620, a sampling capacitor 630, a current cell circuit 640, a voltage to current converter 680a and a tuning circuit 500.

The bias generation circuit 610 is connected between a first voltage (for example, the ground voltage VSS in the exemplary embodiment shown in FIG. 4B) and a second voltage (for example, the power supply voltage VDDA in the exemplary embodiment shown in FIG. 4B). The bias generation circuit 610 generates a bias voltage VBN. The bias generation circuit 610 includes an n-channel metal-oxide semiconductor (NMOS) transistor 611 and a constant current source 612. The NMOS transistor 611 includes a source connected to the ground voltage VSS, a gate connected to a first node N51 and a drain connected to the constant current source 612. Drain of the NMOS transistor 611 is also connected to the first node N51. A reference current IREF flows from the constant current source 612 to the NMOS transistor 611. Therefore, a voltage at the first node N51 is corresponds to the bias voltage VBN due to the reference current IREF.

The transferring switch 620 is connected between the first node N51 and a sampling node SN2, and transfers the bias voltage VBN to the sampling node SN2 in response to a switching control signal SCS1.

The sampling capacitor 330 is connected between the sampling node SN1 and the ground voltage VSS, and samples the bias voltage VBN to provide a sampled bias voltage VBNS.

The current cell circuit 640 may include a switching code controller 650 and a plurality of current cells 661~66$k$.

The switching code controller 650 provides each of a plurality of switching code pairs (SL1, SL1B)~(SL$k$, SL$k$B) to corresponding one of the current cells 661~66$k$, in response to a second switching control signal SCS2. That is, the switching code controller 650 provides a switching code pair (SL1, SL1B) to current cell 661, a switching code pair (SL2, SL2B) to a current cell 662, . . . , and a switching code pair (SL$k$, SL$k$B) to current cell 66$k$. The current cells 661-66$k$ are connected between the sampling node SN2 and a first output node NO3, and each of the current cells 661~66$k$ draws a corresponding cell current 101 from the first output node NO3, in response to the sampled bias voltage VBPS and corresponding one of the switching code pairs (SL1, SL1B)~(SL$k$, SL$k$B) The cell currents IO are summed to a ramping current IRD1 at the first output node NO3.

Each of the current cells 661-66$k$ includes a first NMOS transistor 671, a second NMOS transistor 672, and a third NMOS transistor 673. The first NMOS transistor 671 has a source connected to the ground voltage VSS, a gate connected to the sampling node SN2 and a drain connected to a second node N52. The second NMOS transistor 672 has a source connected to the second node N52, a gate to receive a first switching code SL1 of the switching code pair (SL1, SL1B) and a drain connected to the first output node NO3. The third NMOS transistor 673 has a source connected to the second node N52, a gate to receive a first switching code SL1B of the switching code pair (SL1, SL1B) and a drain connected to the power supply voltage VDDA. The first through third NMOS transistors 671~673 may be also referred to as first through third transistors, respectively. In this case, the drain may be referred to as a first electrode and the source may be referred to as a second electrode.

The current to voltage converter 680$a$ includes a first load resistor RRD1 connected between the power supply voltage VDDA and the first output node NO3 and converts the ramping current IRD1 to a corresponding ramp signal VR.

Figure 5:
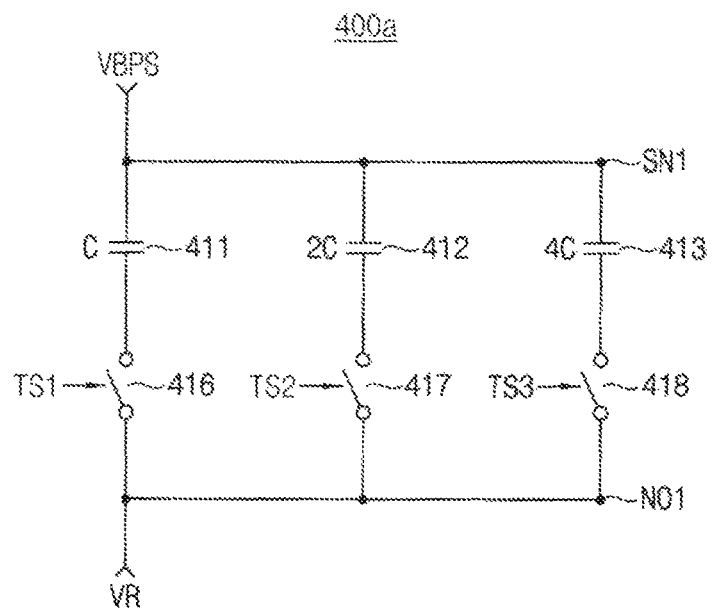
FIG. 5 is a circuit diagram illustrating an example of a tuning circuit of the ramp signal generator in FIG. 4A, according to exemplary embodiments.

FIG. 5 is a circuit diagram illustrating an example of the tuning circuit in FIG. 4A according to exemplary embodiments.

Referring to FIG. 5, a tuning circuit 400$a$ includes a plurality of capacitors 411, 412 and 413 and a plurality of switches 416, 417 and 418. The capacitors 411, 412 and 413 are connected to the sampling node SN1 in parallel with respect to each other and have different capacitances according to multiples of two with respect to each other. For example, capacitor 411 may have capacitance C, capacitor 412 may have capacitance 2C, and capacitor 413 may have capacitance 4C. Each of the switches 416, 417 and 418 is connected between a corresponding one of the capacitors 411, 412 and 413 and the first output node NO1 in parallel with respect to each other and each of the switches 416, 417 and 418 receives a corresponding bit of bits TS1, TS2 and TS3 of the tuning signal TS, as shown in FIG. 5. Each of the switches 416, 417 and 418 is selectively closed in response to one of the bits TS1, TS2 and TS3 of the tuning signal TS and may adjust a degree of the coupling of the sampled bias voltage VBPS to the ramp signal VR. In FIG. 5, a number of the capacitors 411, 412 and 413 and a number of the switches 416, 417 and 418 corresponding respectively to the capacitors 411, 412 and 413 may be varied, which is similar in FIGS. 6 through 9. That is, although three capacitors and three switches are shown in FIG. 5, the number may be more or less than three in other exemplary embodiments, and is not particularly limited.

Figure 6:
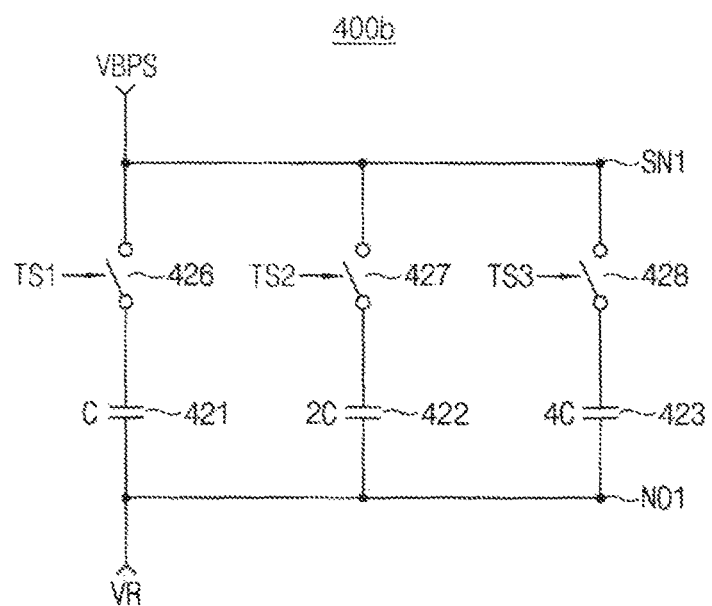
FIG. 6 is a circuit diagram illustrating another example of a tuning circuit of the ramp signal generator in FIG. 4A, according to exemplary embodiments.

FIG. 6 is a circuit diagram illustrating another example of the tuning circuit in FIG. 4A according to exemplary embodiments.

Referring to FIG. 6, a tuning circuit 400$b$ includes a plurality of switches 426, 427 and 428 and a plurality of capacitors 421, 422 and 423. The capacitors 421, 422 and 423 are connected to the first output node NO1 in parallel with respect to each other and have different capacitances according to multiples of two with respect to each other. Each of the switches 426, 427 and 428 is connected between a corresponding one of the capacitors 421, 422 and 423 and the sampling node SN1 in parallel with respect to each other and each of the switches 426, 427 and 428 receives a corresponding bit of bits TS1, TS2 and TS3 of the tuning signal TS. Each of the switches 426, 427 and 428 is selectively closed in response to one of the bits TS1, TS2 and TS3 and may adjust a degree of coupling of the sampled bias voltage VBPS to the ramp signal VR.

Figure 7A:
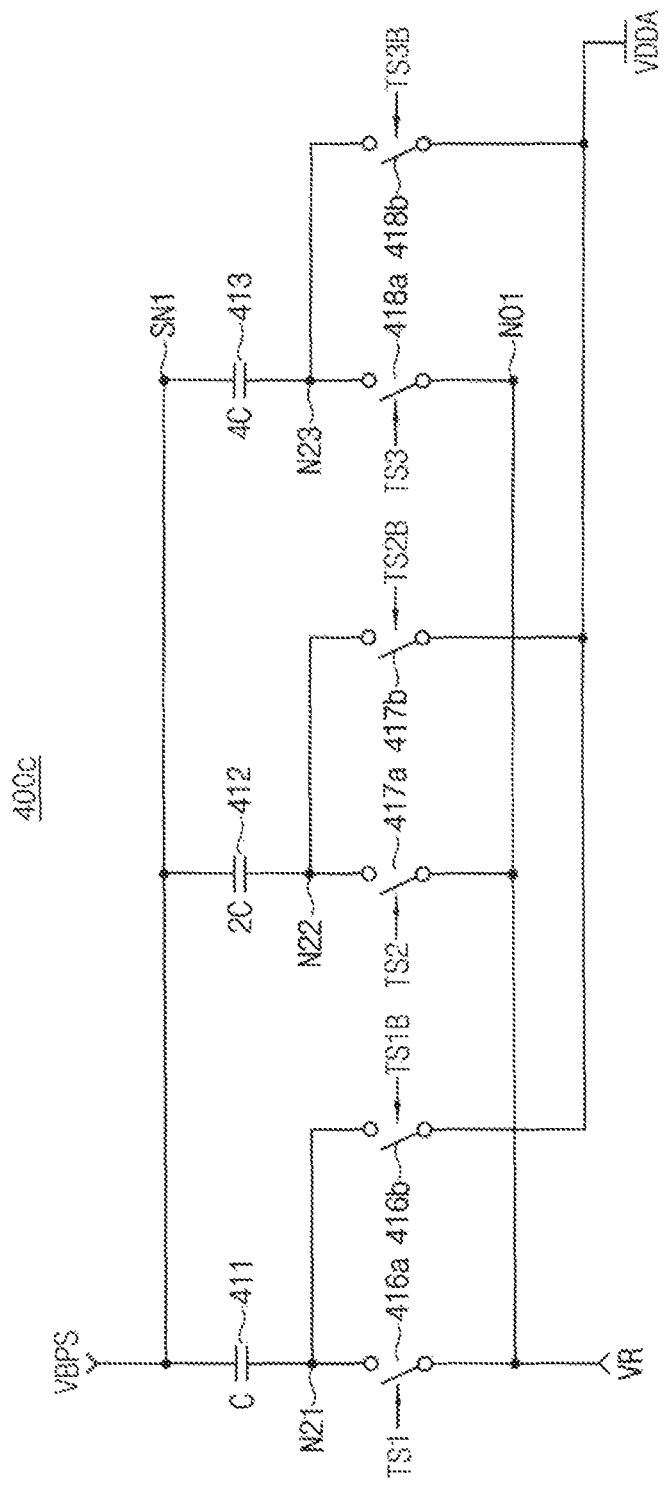
FIG. 7A is a circuit diagram illustrating another example of a tuning circuit of the ramp signal generator in FIG. 4A, according to exemplary embodiments.

FIG. 7A is a circuit diagram illustrating another example of the tuning circuit in FIG. 4A according to exemplary embodiments.

Referring to FIG. 7A, a tuning circuit 400$c$ includes a plurality of capacitors 411, 412 and 413, a plurality of first switches 416$a$, 417$a$ and 418$a$ and a plurality of second switches 416$b$, 417$b$ and 418$b$. Each of the capacitors 411, 412 and 413 is connected between the sampling node SN1 and one of the nodes N21, N22 and N23 in parallel with respect to each other and the capacitors 411, 412 and 413 have different capacitances according to multiples of two with respect to each other. Each of the first switches 416$a$, 417$a$ and 418$a$ is connected between a corresponding one of the capacitors 411, 412 and 413 at a corresponding one of the nodes N21, N22 and N23 and the first output node NO1. Each of the second switches 416$b$, 417$b$ and 418$b$ is connected between a corresponding one of the capacitors 411, 412 and 413 at a corresponding one of the nodes N21, N22 and N23 and the power supply voltage VDDA in parallel with respect to each other. Each of the first switches 416$a$, 417$a$ and 418$a$ receives a corresponding one of bits TS1, TS2 and TS3 of the tuning signal TS and each of the second switches 416$b$, 417$b$ and 418$b$ receives a corresponding one of bits TS1B, TS2B and TS3B of an inverted version of the tuning signal TS. That is, TSxB denotes an inverted TSx. At least one of the first switches 416a, 417a and 418a and at least one of the second switches 416b, 417b and 418b is selectively connected in response to the bits TS1, TS2 and TS3 and the bits TS1B, TS2B and TS3B and may adjust a degree of coupling of the sampled bias voltage VBPS to the ramp signal VR.

FIG. 7B is a circuit diagram illustrating another example of the tuning circuit in FIG. 4A according to exemplary embodiments.

Referring to FIG. 7B, a tuning circuit 400c a includes a plurality of capacitors 411, 412 and 413, a plurality of first switches 416a, 417a and 418a and a plurality of second switches 416b, 417b and 418b. Each of the capacitors 411, 412 and 413 is connected between the first output node NO1 and one of the nodes N211, N221 and N231 in parallel with respect to each other and the capacitors 411, 412 and 413 have different capacitances according to multiples of two with respect to each other. Each of the first switches 416a, 417a and 418a is connected between a corresponding one of the capacitors 411, 412 and 413 at a corresponding one of the nodes N211, N221 and N231 and the sampling node SN1 in parallel with respect to each other. Each of the second switches 416b, 417b and 418b is connected between a corresponding one of the capacitors 411, 412 and 413 at a corresponding one of the nodes N21, N22 and N23 and the ground voltage VSS in parallel with respect to each other. Each of the first switches 416a, 417a and 418a receives a corresponding one of bits TS1, TS2 and TS3 of the tuning signal TS and each of the second switches 416b, 417b and 418b receives a corresponding one of bits TS1B, TS2B and TS3B of an inverted version of the tuning signal TS. At least one of the first switches 416a, 417a and 418a and at least one of the second switches 416b, 417b and 418b is selectively connected in response to the bits TS1, TS2 and TS3 and the bits TS1B, TS2B and TS3B and may adjust a degree of coupling of the sampled bias voltage VBPS to the ramp signal VR.

Figure 8:
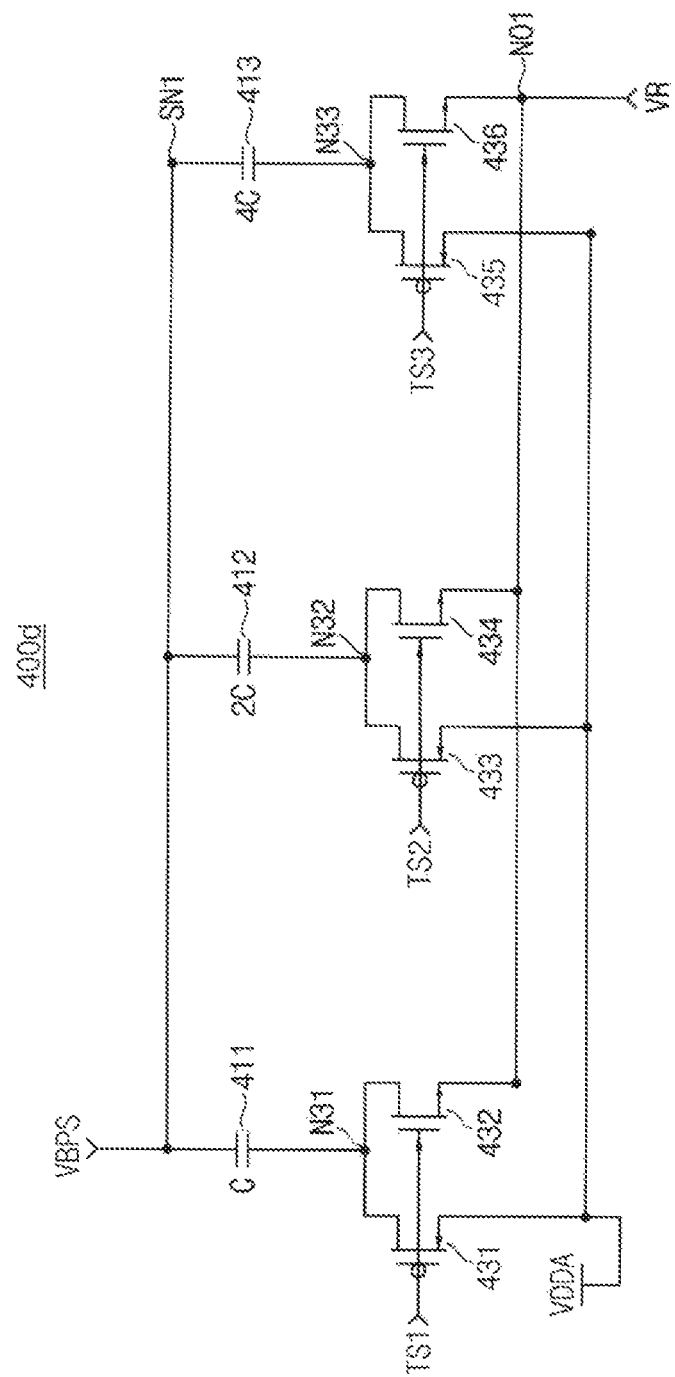
FIG. 8 is a circuit diagram illustrating another example of a tuning circuit of the ramp signal generator in FIG. 4A, according to exemplary embodiments.

FIG. 8 is a circuit diagram illustrating another example of the tuning circuit in FIG. 4A according to exemplary embodiments.

Referring to FIG. 8, a tuning circuit 400d includes a plurality of capacitors 411, 412 and 413, a plurality of PMOS transistors 431, 433 and 435, and a plurality of NMOS transistors 432, 434 and 436. Each of the capacitors 411, 412 and 413 is connected between the sampling node SN1 and one of the nodes N31, N32 and N33 in parallel with respect to each other and the capacitors 411, 412 and 413 have different capacitances according to multiples of two with respect to each other. Each of the PMOS transistors 431, 433 and 435 is connected between a corresponding one of the capacitors 411, 412 and 413 at a corresponding one of the nodes N31, N32 and N33 and the power supply voltage VDDA in parallel with respect to each other. Each of the NMOS transistors 432, 434 and 436 is connected between a corresponding one of the capacitors 411, 412 and 413 at a corresponding one of the nodes N31, N32 and N33 and the first output node NO1 in parallel with respect to each other. Each gate of PMOS transistors 431, 433 and 435 receives a corresponding one of bits TS1, TS2 and TS3 of the tuning signal TS and each gate of the NMOS transistors 432, 434 and 436 receives a corresponding one of bits TS1, TS2 and TS3 of the tuning signal TS. At least one of the PMOS transistors 431, 433 and 435 and at least one of the NMOS transistors 432, 434 and 436 is selectively turned-on in response to the bits TS1, TS2 and TS3 and may adjust a degree of coupling of the sampled bias voltage VBPS to the ramp signal VR.

Figure 9:
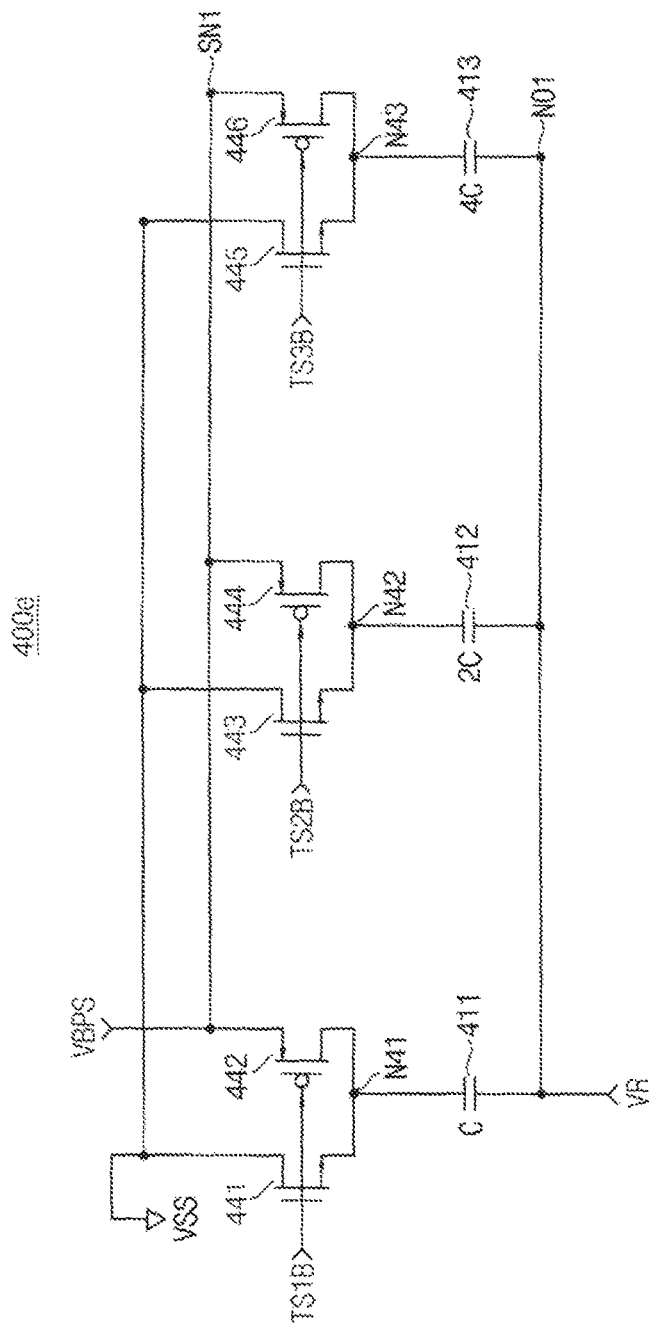
FIG. 9 is a circuit diagram illustrating another example of a tuning circuit of the ramp signal generator in FIG. 4A, according to exemplary embodiments.

FIG. 9 is a circuit diagram illustrating another example of the tuning circuit in FIG. 4A according to exemplary embodiments.

Referring to FIG. 9, a tuning circuit 400e includes a plurality of capacitors 411, 412 and 413, a plurality of NMOS transistors 441, 443 and 445, and a plurality of PMOS transistors 442, 444 and 446. Each of the capacitors 411, 412 and 413 is connected between the first output node NO1 and one of the nodes N41, N42 and N43 in parallel with respect to each other and the capacitors 411, 412 and 413 have different capacitances according to multiples of two with respect to each other. Each of the NMOS transistors 441, 443 and 445 is connected between a corresponding one of the capacitors 411, 412 and 413 at a corresponding one of the nodes N41, N42 and N43 and the ground voltage VSS in parallel with respect to each other. Each of the PMOS transistors 442, 444 and 446 is connected between a corresponding one of the capacitors 411, 412 and 413 at a corresponding one of the nodes N41, N42 and N43 and the sampling node SN1 in parallel with respect to each other. Each gate of the NMOS transistors 441, 443 and 445 receives a corresponding one of bits TS1B, TS2B and TS3B of an inverted version of the tuning signal TS and each gate of the PMOS transistors 442, 444 and 446 receives a corresponding one of the bits TS1B, TS2B and TS3B. At least one of the NMOS transistors 441, 443 and 445 and at least one of the PMOS transistors 442, 444 and 446 is selectively turned-on in response to the bits TS1B, TS2B and TS3B and may adjust a degree of coupling of the sampled bias voltage VBPS to the ramp signal VR.

The tuning circuit 400 in FIG. 4A may employ one of one of the tuning circuits 400a, 400b, 400c, 400ca, 400d and 400e of FIGS. 5 through 9. Similarly, the tuning circuit 500 in FIG. 4B may employ one of the tuning circuits 400a, 400b, 400c, 400ca, 400d and 400e of FIGS. 5 through 9.

Figure 10:
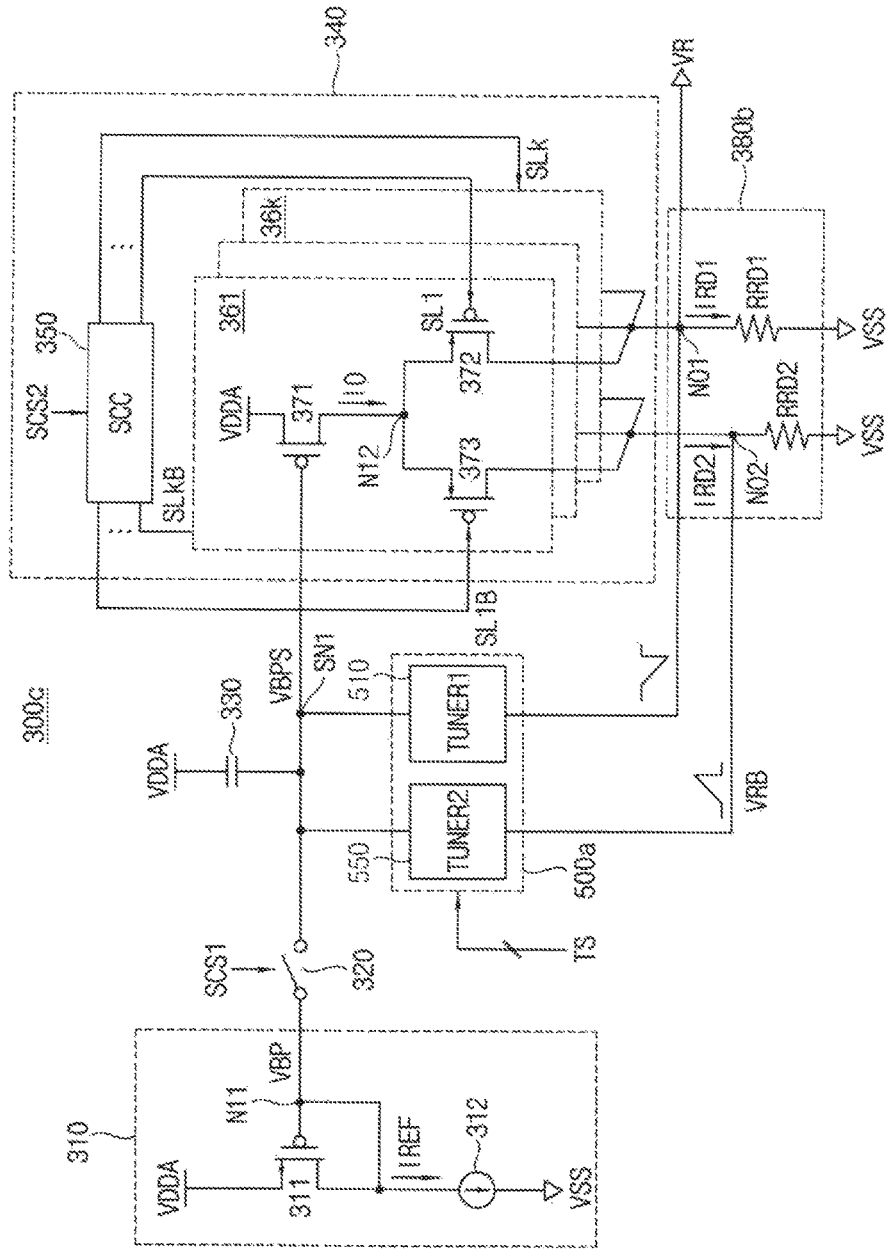
FIG. 10 is a circuit diagram illustrating another example of a ramp signal generator in the image sensor of FIG. 1, according to exemplary embodiments.

FIG. 10 is a circuit diagram illustrating another example of the ramp signal generator in the image sensor of FIG. 1 according to exemplary embodiments.

A ramp signal generator 300c of FIG. 10 is different from the ramp signal generator 300a of FIG. 4A in a configuration of a current to voltage converter 380b and a configuration of a tuning circuit 500a. Therefore, the description below will focus on the current to voltage converter 380b and the tuning circuit 500a.

Referring to FIG. 10, the current to voltage converter 380b includes a first load resistor RRD1 and a second load resistor RRD2. The first load resistor RRD1 is connected between the first output node NO1 and the ground voltage VSS and the second load resistor RRD2 is connected between a second output node NO2 and the ground voltage VSS. The tuning circuit 500a may include a first tuner 510 and a second tuner 550. The first tuner 510 is connected between the first output node NO1 and the sampling node SN1 and the second tuner 550 is connected between the second output node NO2 and the sampling node SN1.

The first load resistor RRD1 converts a first ramping current IRD1 to the corresponding ramp signal VR and the second load resistor RRD2 converts a second ramping current IRD2 to a corresponding second ramp signal VRB. Since, each of the first switching codes SL1~SLk has a logic level complementary with a corresponding one of the second switching codes SL1B~SLkB, the first ramping current IRD1 and the second ramping current IRD2 have complementary ramping directions with respect to each other. When the ramp signal VR is down-ramping, the second ramp signal VRB is up-ramping. Alternatively, when the ramp signal VR is up-ramping, the second ramp signal VRB is down-ramping.

The first tuner 510 includes at least one capacitor connected between the first output node NO1 and the sampling node SN1, and couples the sampled bias voltage VBPS to the ramp signal VR to adjust a degree of nonlinearity of the ramp signal VR. In addition, the second tuner 550 includes at least one capacitor connected between the second output node NO2 and the sampling node SN1, and couples the sampled bias voltage VBPS to the second ramp signal VRB to adjust a degree of nonlinearity of the second ramp signal VRB. The first tuner 510 may employ one of the tuning circuits 400a, 400b, 400c, 400ca, 400d and 400e of FIGS. 5 through 9, and the second tuner 550 may employ one of the tuning circuits 400a, 400b, 400c, 400ca, 400d and 400e of FIGS. 5 through 9, which corresponds to the first tuner 510.

Figure 11:
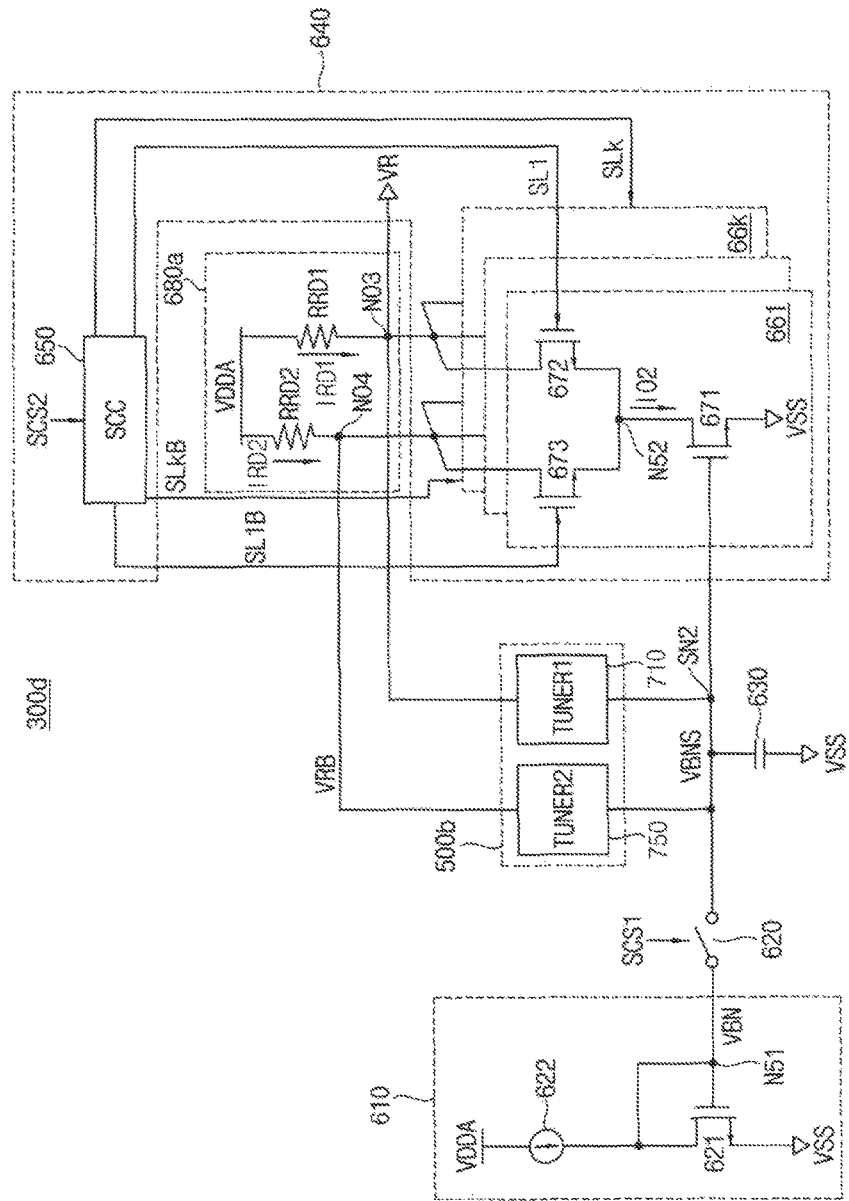
FIG. 11 is a circuit diagram illustrating another example of a ramp signal generator in the image sensor of FIG. 1, according to exemplary embodiments.

FIG. 11 is a circuit diagram illustrating another example of the ramp signal generator in the image sensor of FIG. 1 according to exemplary embodiments.

A ramp signal generator 300d of FIG. 11 is different from the ramp signal generator 300b of FIG. 4B in a configuration of a current to voltage converter 680a and a configuration of a tuning circuit 500b. Therefore, the description below will focus on the current to voltage converter 680a and the tuning circuit 500b.

Referring to FIG. 11, the current to voltage converter 680b includes a first load resistor RRD1 and a second load resistor RRD2. The first load resistor RRD1 is connected between the power supply voltage VDDA and the first output node NO3 and the second load resistor RRD2 is connected between the power supply voltage VDDA and a second output node NO4. The first load resistor RRD1 converts a first ramping current IRD1 to the corresponding ramp signal VR and the second load resistor RRD2 converts a second ramping current IRD2 to a corresponding second ramp signal VRB.

The tuning circuit 500b may include a first tuner 710 and a second tuner 750. The first tuner 710 is connected between the first output node NO3 and the sampling node SN2 and the second tuner 750 is connected between the second output node NO4 and the sampling node SN2.

As is described with reference to FIG. 10, the first tuner 710 includes at least one capacitor connected between the first output node NO3 and the sampling node SN2, and couples the sampled bias voltage VBNS to the ramp signal VR to adjust a degree of nonlinearity of the ramp signal VR. In addition, the second tuner 750 includes at least one capacitor connected between the second output node NO4 and the sampling node SN2, and couples the sampled bias voltage VBNS to the second ramp signal VRB to adjust a degree of nonlinearity of the second ramp signal VRB. The first tuner 710 may employ one of the tuning circuits 400a, 400b, 400c, 400ca, 400d and 400e of FIGS. 5 through 9, and the second tuner 750 may employ one of the tuning circuits 400a, 400b, 400c, 400ca, 400d and 400e of FIGS. 5 through 9, which corresponds to the first tuner 510.

Figure 12:
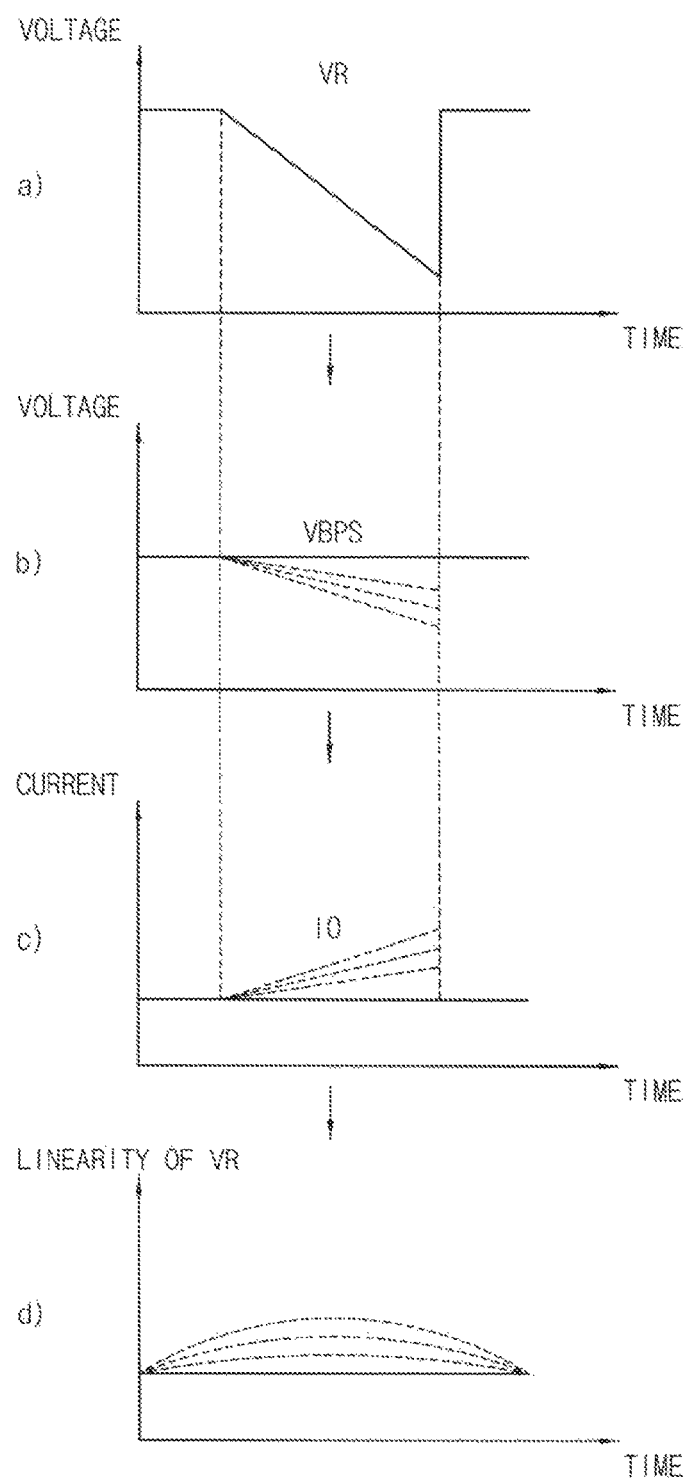
FIG. 12 illustrates that the tuning circuit according to exemplary embodiments adjusts a degree of nonlinearity of the ramp signal.

FIG. 12 illustrates that the tuning circuit according to exemplary embodiments adjusts a degree of the nonlinearity of the ramp signal.

FIG. 12 illustrates an example in which the tuning circuit adjusts a degree of the nonlinearity of a ramp signal that is down-ramping.

In FIG. 12, a) denotes the ramp signal VR that is down-ramping, and b) denotes that the sampled bias voltage VBPS is coupled to the ramp signal VR by one of the tuning circuit 400 in FIG. 4A, the tuning circuit 500a of FIG. 10 and the tuning circuit 500b in FIG. 11 and the degree of coupling is adjusted in response to the tuning signal TS. When the sampled bias voltage VBPS is coupled to the ramp signal VR as b) illustrates, the sampled bias voltage VBPS follows the ramp signal VR, and the cell current I0 output from the PMOS transistor 371 changes as is illustrated by c). When the cell current I0 is output as illustrated in c), a nonlinear characteristic of the ramp signal VR is generated to cancel the nonlinearity of FIG. 3B. Therefore, linearity of the ramp signal VR may be increased.

Figure 13:
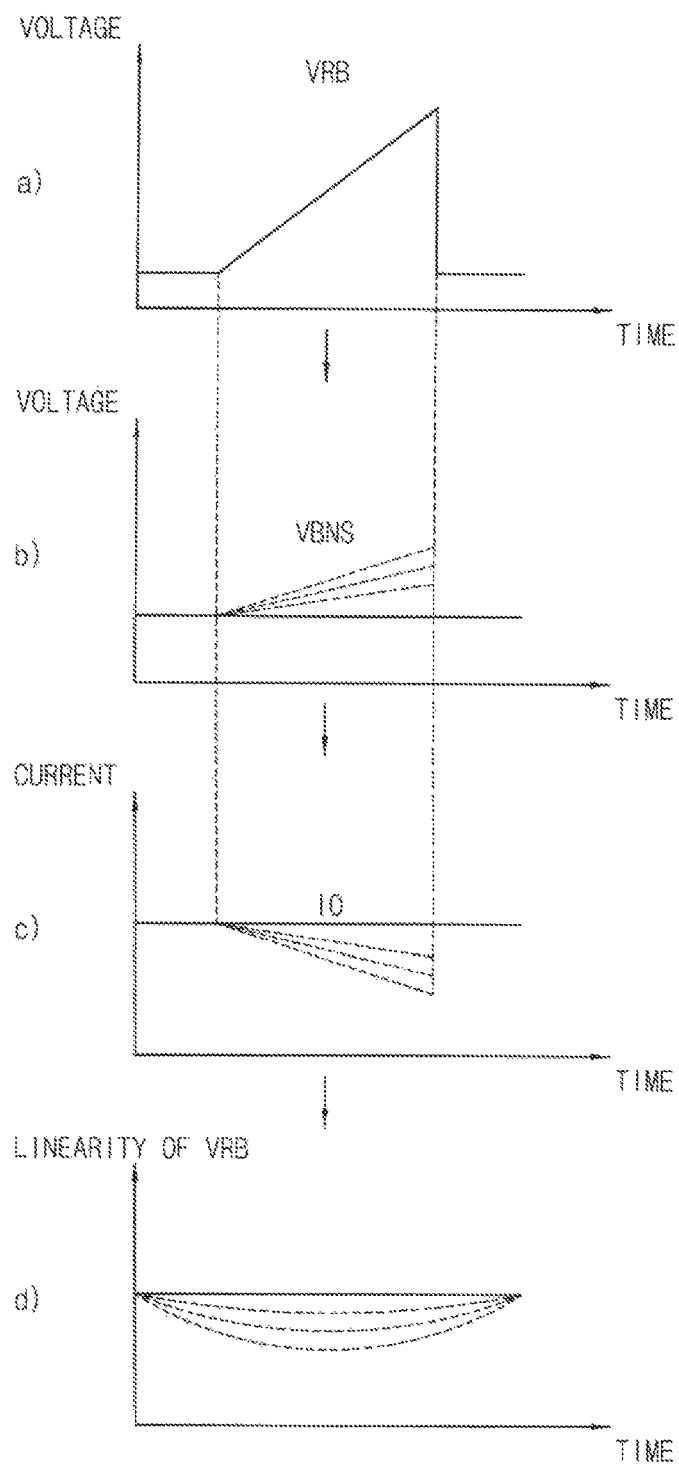
FIG. 13 illustrates that the tuning circuit according to exemplary embodiments adjusts a degree of nonlinearity of a second ramp signal.

FIG. 13 illustrates that the tuning circuit according to exemplary embodiments adjusts a degree of the nonlinearity of the second ramp signal.

FIG. 13 illustrates an example in which the tuning circuit adjusts degree of the nonlinearity of a second ramp signal that is up-ramping.

In FIG. 13, a) denotes the second ramp signal VRB that is up-ramping, and b) denotes that the sampled bias voltage VBNS is coupled to the second ramp signal VRB by one of the tuning circuit 400 in FIG. 4A, the tuning circuit 500a of FIG. 10 and the tuning circuit 500b in FIG. 11 and the degree of coupling is adjusted in response to the tuning signal TS. When the sampled bias voltage VBNS is coupled to the second ramp signal VRB as b) illustrates, the sampled bias voltage VBNS follows the second ramp signal VRB, and the cell current I0 output from the PMOS transistor 371 changes as is illustrated by c). When the cell current I0 is output as illustrated in c), nonlinear characteristic of the second ramp signal VRB is generated to cancel the nonlinearity of FIG. 3B. Therefore, linearity of the second ramp signal VRB is more increased.

In FIGS. 12 and 13, the degree of coupling of the sampled bias voltage VBPS to the ramp signal VR or the degree of coupling of the sampled bias voltage VBNS to the second ramp signal VRB may be determined based on a result of testing a nonlinearity of the ramp signal VR of FIG. 3B. The result of testing may be stored in the register 290 in FIG. 1, and the timing controller 210 may provide the second control signal CTL2 to the ramp signal generator 300 such that the degree of the nonlinearity of the ramp signal VR of FIG. 3B is cancelled. In addition, the ramp signal generator 300 may provide the tuning signal TS to the tuning circuit 400 in response to the second control signal CTL2.

Figure 14:
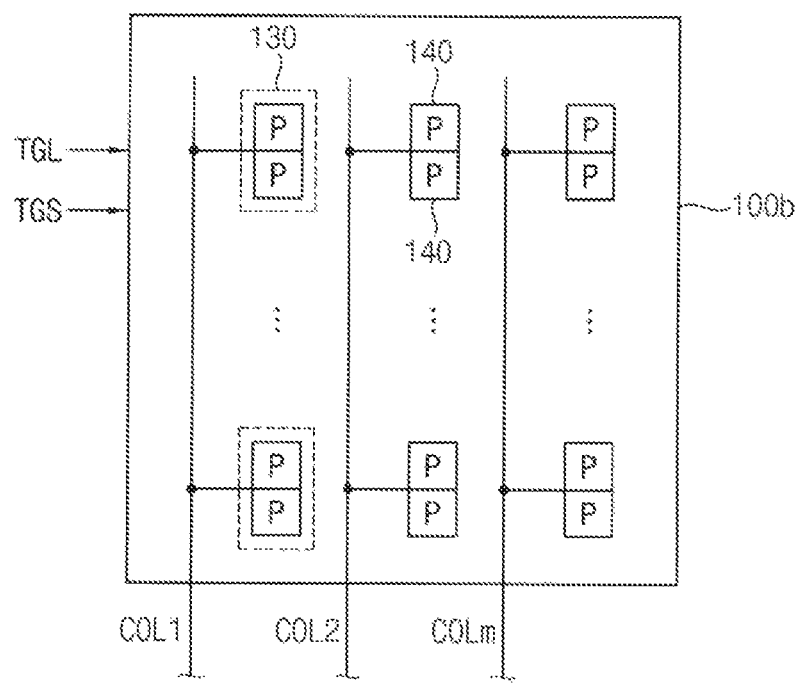
FIG. 14 illustrates another example of the pixel array in the image sensor of FIG. 1 according to exemplary embodiments.

FIG. 14 illustrates another example of the pixel array in the image sensor of FIG. 1 according to exemplary embodiments.

Referring to FIGS. 1 and 14, a pixel array 100b may include a plurality of pixels 140 arranged in rows and columns. The row driver 220 may control operation of the pixels 140 through a long exposure transmission control signal TGL and a short exposure transmission control signal TGS instead of the transmission control signal TG in FIG. 1. The row driver 220 may activate the long exposure transmission control signal TGL and the short exposure transmission control signal TGS at the same time. An activated duration of the long exposure transmission control signal TGL may be relatively long, and an activated duration of the short exposure transmission control signal TGS may be relatively short.

Two pixels 130 adjacent to each other in a column direction may include the photoelectric conversion element PD and the transfer transistor TX, respectively and may share the reset transistor RX, the floating diffusion region FD, the source follower SF and the selection transistor SX in the configuration of the pixel of FIG. 2.

Figure 15:
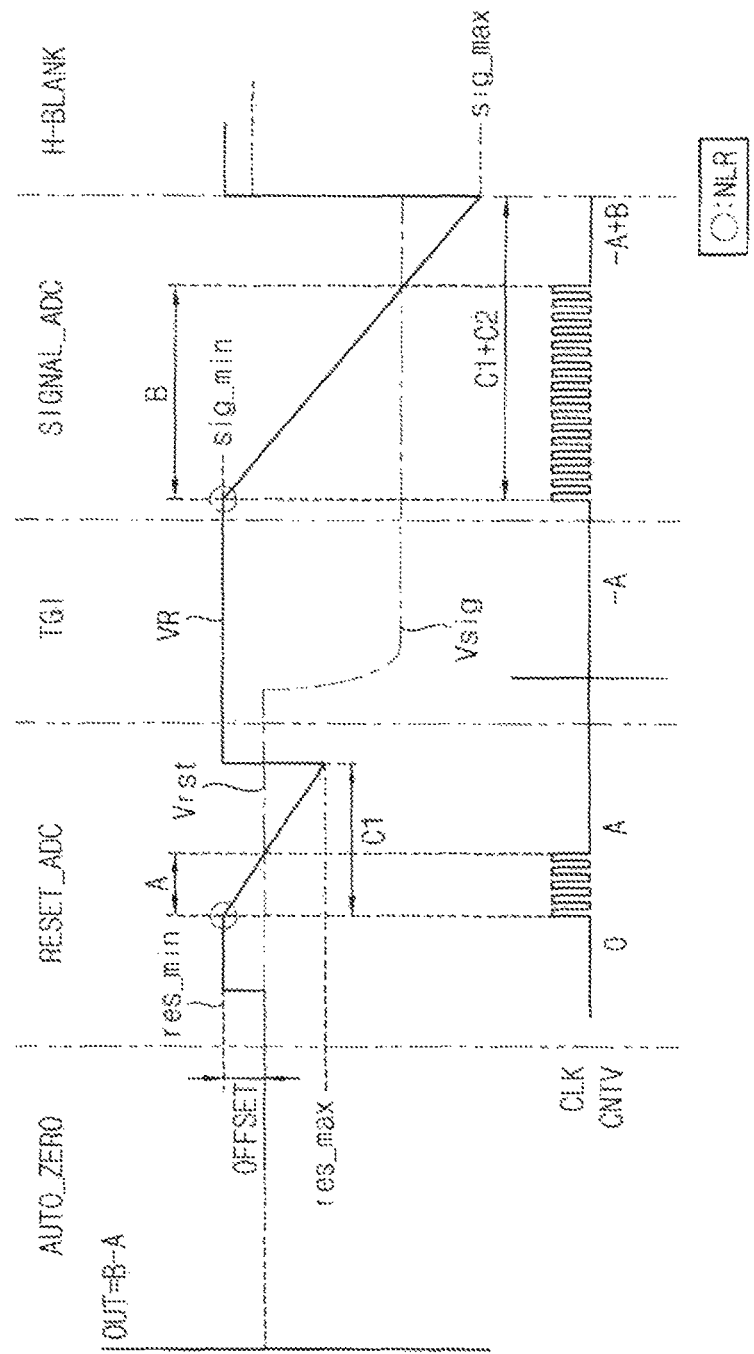
FIG. 15 is a diagram for explaining analog to digital (AD) conversion performed based on a ramp signal in the image sensor of FIG. 1, according to exemplary embodiments.

FIG. 15 is a diagram for explaining AD conversion performed based on a ramp signal in the image sensor of FIG. 1.

A pixel signal output from the pixel 110 may include a reset signal Vrst and an image signal Vsig.

A 1-horizontal time may include an auto zero period AUTO_ZERO, a reset signal AD conversion (ADC) period RESET_ADC, a transfer control signal enabling period TGI, an image signal ADC period SIGNAL_ADC, and a horizontal blank period H-BLANK. When a frame rate is Z (where Z is a natural number of at least 2), the 1-horizontal time may be defined as 1/(Z*n), where "n" may be the number of rows in the pixel array 100.

The 1-horizontal time may refer to a time to convert pixel signals corresponding to a line or pixel signals output from pixels in a row from an analog format into a digital format.

The auto zero period AUTO_ZERO may be a duration (or interval) to determine a decision point of each of the comparators 241 through 24m included in the comparator circuit 240. The decision point may be for ADC, and the auto zero period AUTO_ZERO may be a duration to store or determine an offset of each of the comparators 241 through 24m.

The reset signal ADC period RESET_ADC may be a duration in which the reset signal Vrst is converted into a digital signal based on the ramp signal VR. The transfer control signal enabling period TGI may be a duration while the transfer control signal TG is enabled.

The image signal ADC period SIGNAL_ADC may be a duration while the image signal Vsig is converted into a digital signal based on the ramp signal VR. The horizontal blank period H-BLANK may be a duration while ADC for the next line is prepared. The reset signal ADC period RESET_ADC may be simply referred to as a "reset signal period" and the image signal ADC period SIGNAL_ADC may be simply referred to as an "image signal period.

FIG. 15 illustrates an example of the determination from a low code using a ramp signal VR that is down-ramping.

"OFFSET" may denote an offset of the ramp signal VR. In the below description, the counter 251 may generically refer to the counters 251, 252, through 25m, and the memory 261 may generically refer to the memories 261, 262, through 26m. The comparator 241 may refer to the comparators 241, 242, through 24m.

A reference character C1 may denote the maximum cycle of the clock signal CLK applied to the counter 251 during the reset signal ADC period RESET_ADC and "C1+C2" may denote the maximum cycle of the clock signal CLK applied to the counter 251 during the image signal ADC period SIGNAL_ADC. When C1 is 256, C2 may be 1024, but these are just examples.

Referring to FIGS. 1 and 15, the ramp signal generator 300 may output the ramp signal VR that (monotonously) decreases over time from a second level corresponding to a minimum reset counting value res_min of the counter 251 down to a first level corresponding to a maximum reset counting value res_max of the counter 251 during the reset signal ADC period RESET_ADC. At this time, the ramp signal VR is referred to as a down-ramping ramp signal.

The counter 251 may generate the counting value CNTV that increases sequentially from "0" to "A" in response to the clock signal CLK and a comparison signal output from the comparator 241 until the level of the reset signal Vrst is equal to the level of the ramp signal VR. The memory 261 may store "A" as the counting value CNTV generated by the counter 251. In other words, when the level of the reset signal Vrst is the same as the level of the ramp signal VR, the counter 251 may hold "A" as the counting value CNTV.

The pixel 110 may output a pixel signal corresponding to the image signal Vsig during the transfer control signal enabling period TGI. The counter 251 or the memory 261 may generate "-A", i.e., ones' complement of "A", during the transfer control signal enabling period TGI. A method of generating "-A" in the image sensor 10 may be variously modified in different exemplary embodiments. The ramp signal generator 300 may output the ramp signal VR that (monotonously) decreases over time from a fourth level corresponding to a minimum image signal counting value sig_min of the counter 251 down to a third level corresponding to a maximum image signal counting value sig_max of the counter 251 during the image signal ADC period SIGNAL_ADC.

The counter 251 may generate the counting value CNTV that increases sequentially from "-A" to "B" in response to the clock signal CLK and a comparison signal output from the comparator 241 until the level of the image signal Vsig is equal to the level of the ramp signal VR. The memory 261 may store a counting value corresponding to "-A+B" as the counting value CNTV. Accordingly, the output circuit 880 may output the final counting value OUT (=B-A).

The image sensor 10 using single-slope ADC may perform ADC sequentially from a low code, as shown in FIG. 15. Nonlinearity of a low code region may be amplified and increased due to gamma gain or the like. It takes a lot of time for an output signal of the comparator 241 or a pixel signal of the pixel 110 to be stabilized right after the auto zero period AUTO_ZERO (or right before the reset signal ADC period RESET_ADC) or right after the transfer control signal enabling period TGI (or right before the image signal ADC period SIGNAL_ADC).

When ADC is performed on the pixel signal of the pixel 110 in a state where the output signal of the comparator 241 or the pixel signal of the pixel 110 has not been stabilized, a nonlinear ADC value may be output from the low code region.

In FIG. 15, "NLR" (i.e., circles in the RESET_ADC period and the SIGNAL_ADC period) denotes a nonlinear region.

According to exemplary embodiments, the ramp signal generator 400 couples the sampled bias voltage VBPS to the ramp signal VR through the tuning circuit 400, and thus artificially generates a nonlinear characteristic of the ramp signal VR that, when applied to the nonlinear characteristic of the ramp signal VR, cancels the nonlinearity occurring in the nonlinear region in FIG. 15. Therefore, ramp signal generator 400 may increase a linearity of the ramp signal VR.

Figure 16:
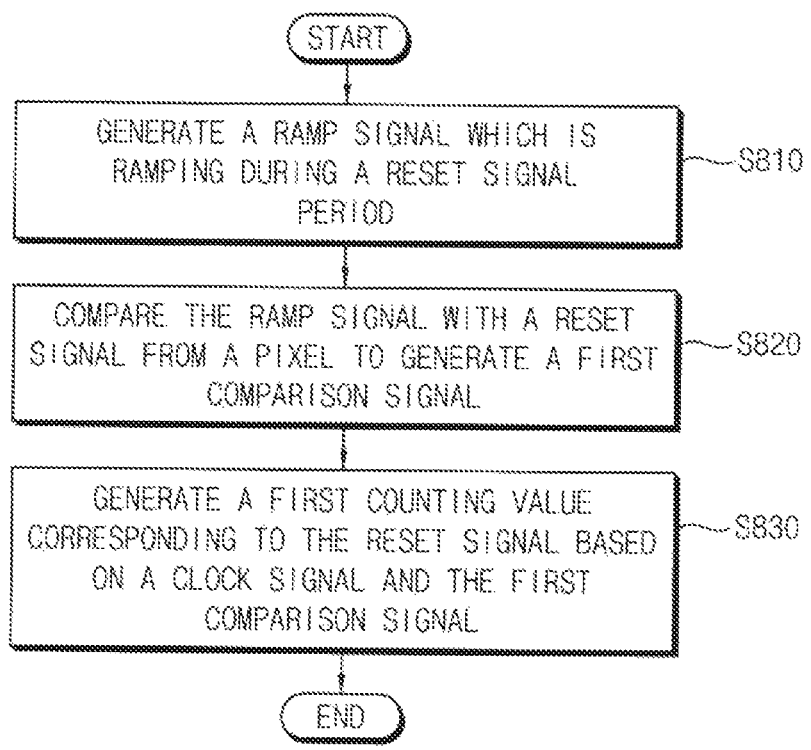
FIG. 16 is a flow chart illustrating a method of operating an image sensor according to exemplary embodiments.

FIG. 16 is a flow chart illustrating a method of operating an image sensor according to exemplary embodiments.

Referring to FIGS. 1 through 16, in a method of operating an image sensor 10, the ramp signal generator 300 generates the ramp signal VR that is ramping during the reset signal ADC period RESET_ADC (S810). When generating the ramp signal VR, the ramp signal generator 400 couples the sampled bias voltage VBPS to the ramp signal VR through the tuning circuit 400, and thus artificially generates a nonlinear characteristic of the ramp signal VR that, when applied to the ramp signal VR, cancels the nonlinearity occurring in the nonlinear region in FIG. 15 so as to increase a linearity of the ramp signal VR as described with reference to FIGS. 4 through 14.

The comparator 241 compares the reset signal Vrst output from the pixel 110 and the ramp signal VR to generate a first comparison signal (S820).

The counter 251 of the counter circuit 250 generates a first counting value CNTV corresponding to the reset signal Vrst based on the clock signal CLK and the first comparison signal (S830).

The ramp signal generator 300 generates the ramp signal VR that is ramping during the image signal ADC period SIGNAL_ADC. The comparator 241 compares the image signal Vsig output from the pixel 110 and the ramp signal VR to generate a second comparison signal. The counter 251 of the counter circuit 251 generates a second counting value CNTV corresponding to the image signal Vsig based on the clock signal CLK and the second comparison signal. While the ramp signal generator 300 generates the ramp signal VR that is ramping during the image signal ADC period SIGNAL_ADC, the counter 251 generates ones' complement of the first counting value CNTV and sums the second counting value CNTV and the ones' complement of the first counting value, and the output circuit 280 outputs the final counting value OUT corresponding to the summed value.

Therefore, in the method of operating the image sensor 10, when the ramp signal VR is generated, the nonlinearity characteristic is cancelled to increase the linearity of the ramp signal VR. Therefore, occurrence of errors in the low code may be reduced and a performance of the image sensor may be enhanced.

Figure 17:
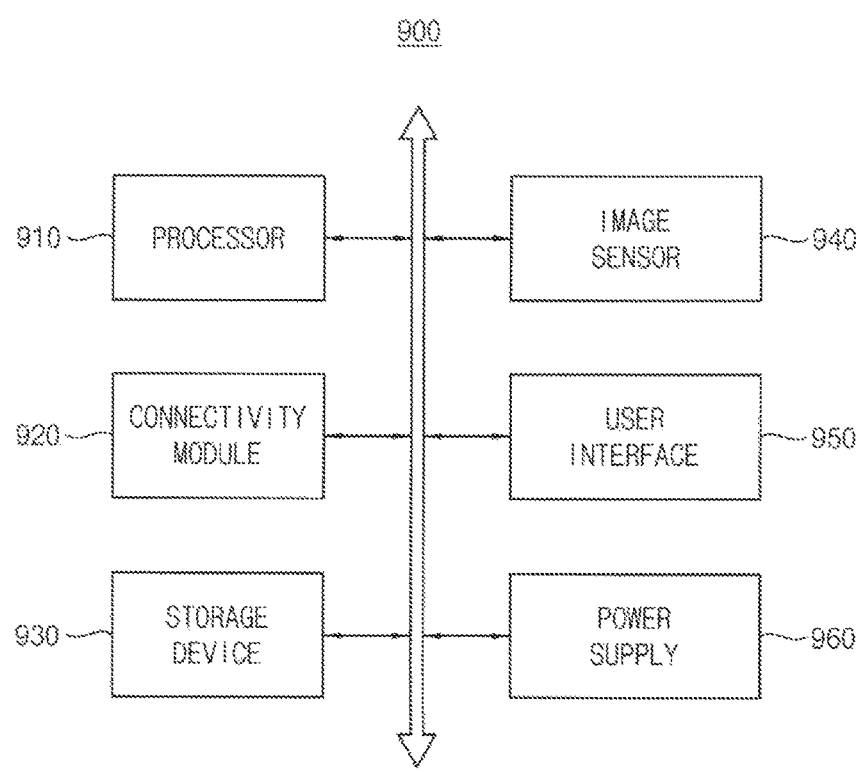
FIG. 17 is a block diagram illustrating a mobile device according to exemplary embodiments.

FIG. 17 is a block diagram illustrating a mobile device according to exemplary embodiments.

Referring to FIG. 17, a mobile device 900 includes a processor 910 and an image sensor 940. The mobile device 900 may further include a connectivity module 920, a storage device 930, a user interface 950 and a power supply 960.

The processor 910 may be one or more microprocessors and controls overall operations of the mobile device 900. The image sensor 940 is controlled by the processor 910 and may be an image sensor according to exemplary embodiments. The image sensor 940 may employ the image sensor 10 of FIG. 1 and may include a ramp signal generator that generates ramp signal. The ramp signal generator may couple a sampled bias voltage to the ramp signal through a tuning circuit, and thus may artificially generate a nonlinear characteristic of the ramp signal to cancel the nonlinearity occurring in a high speed operation of the image sensor 940. Therefore, ramp signal generator may increase a linearity of the ramp signal.

The connectivity module 920 may communicate with an external device (not shown). The storage device 930 may operate as a data storage for data processed by the processor 910 or a working memory in the mobile device 900. The user interface 950 may include at least one input device such as, for example, a keypad, a button, a touch screen, etc., and/or at least one output device such as, for example, a display device, etc. The power supply 960 may provide power to the mobile device 900.

The present disclosure may be applied to various image sensors and various imaging systems. For instance, the present disclosure may be applied to a mobile phone, a smart phone, a personal digital assistant (PDA), a portable multimedia player (PMP), a portable game console, a wearable system, an internet of things (IoT) system, 3D geometry reconstruction system, an array camera system, a virtual reality (VR) system, an augmented reality (AR) system, etc.

According to various exemplary embodiments described herein, a ramp signal generator may couple a sampled bias voltage to a ramp signal through a tuning circuit, and thus may artificially generate a nonlinear characteristic of the ramp signal to cancel the nonlinearity occurring in a high speed operation of the image sensor. Therefore, ramp signal generator may increase a linearity of the ramp signal.

The foregoing is illustrative of exemplary embodiments and is not to be construed as limiting thereof. Although a few exemplary embodiments have been described, those skilled in the art will readily appreciate that many modifications are possible in the exemplary embodiments without materially departing from the novel teachings and advantages of the present disclosure. Accordingly, all such modifications are intended to be included within the scope of the present disclosure as defined in the claims.

What is claimed is:

1. A ramp signal generator of an image sensor, the ramp signal generator comprising:
    a bias generation circuit, connected between a first voltage and a second voltage, configured to generate a bias voltage;
    a transferring switch configured to transfer the bias voltage to a sampling node in response to a first switching control signal;
    a sampling capacitor connected between the first voltage and the sampling node, configured to sample the bias voltage;
    a current cell circuit configured to provide a first output node with a first ramping current during a ramping period, in response to a sampled bias voltage of the sampling node and a plurality of switching code pairs;
    a current to voltage converter including a first load resistor connected between the first output node and the second voltage, wherein the first load resistor is configured to convert the first ramping current to a first ramp signal which is ramping during the ramping period; and
    a tuning circuit connected between the first output node and the sampling node, the tuning circuit including at least one capacitor configured to couple the sampled bias voltage to the first ramp signal, wherein the tuning circuit is configured to adjust a degree of nonlinearity of the first ramp signal in response to a tuning signal.

2. The ramp signal generator of claim 1, wherein the current cell circuit comprises:
    a plurality of current cells connected between the first voltage and the first output node, wherein each of the plurality of current cells is configured to generate a cell current in response to the sampled bias voltage and a corresponding one of the plurality of switching code pairs; and
    a switching code controller configured to provide each of the plurality of switching code pairs to a corresponding one of the plurality of current cells in response to a second switching control signal.

3. The ramp signal generator of claim 2, wherein each of the plurality of current cells comprises:
    a first transistor which has a first electrode connected to the first voltage, a gate connected to the sampling node to receive the sampled bias voltage and a second electrode connected to a first node;
    a second transistor which has a first electrode connected to the first node, a gate to receive a first switching code of a switching code pair and a second electrode connected to the first output node; and
    a third transistor which has a first electrode connected to the first node, a gate to receive a second switching code of the switching code pair and a second electrode connected to the second voltage, wherein the second switching code has a logic level which is complementary with a logic level of the first switching code, wherein a sum of cell currents of the plurality of current cells correspond to the first ramping current.

4. The ramp signal generator of claim 3, wherein:
the first voltage is a power supply voltage;
the second voltage is a ground voltage; and
each of the first transistor, the second transistor and the third transistor is a p-channel metal-oxide (PMOS) transistor.

5. The ramp signal generator of claim 3, wherein:
the first voltage is a ground voltage;
the second voltage is a power supply voltage; and
each of the first transistor, the second transistor and the third transistor is an n-channel metal-oxide (NMOS) transistor.

6. The ramp signal generator of claim 1, wherein the tuning circuit comprises:
a plurality of capacitors connected to the sampling node in parallel with respect to each other, wherein the plurality of capacitors have different capacitances with respect to each other; and
a plurality of switches, wherein each of the plurality of switches is connected between a corresponding one of the plurality of capacitors and the first output node in parallel with respect to each other and each of the plurality of switches receives a corresponding bit of the tuning signal.

7. The ramp signal generator of claim 1, wherein the tuning circuit comprises:
a plurality of capacitors connected to the first output node in parallel with respect to each other, wherein the plurality of capacitors have different capacitances with respect to each other; and
a plurality of switches, wherein each of the plurality of switches is connected between a corresponding one of the plurality of capacitors and the sampling node in in parallel with respect to each other and each of the plurality of switches receives a corresponding bit of the tuning signal.

8. The ramp signal generator of claim 1, wherein the tuning circuit comprises:
a plurality of capacitors connected to the sampling node in parallel with respect to each other, wherein the plurality of capacitors have different capacitances with respect to each other;
a plurality of first switches, wherein each of the plurality of first switches is connected between a corresponding one of the plurality of capacitors and the first output node in in parallel with respect to each other; and
a plurality of second switches, wherein each of the plurality of second switches is connected between a corresponding one of the plurality of capacitors and the first voltage in parallel with respect to each other,
wherein each of the plurality of first switches receives a corresponding bit of the tuning signal and each of the plurality of second switches receives a corresponding bit of an inverted version the tuning signal.

9. The ramp signal generator of claim 1, wherein the tuning circuit comprises:
a plurality of capacitors connected to the first output node in parallel with respect to each other, wherein the plurality of capacitors have different capacitances with respect to each other;
a plurality of first switches, wherein each of the plurality of first switches is connected between a corresponding one of the plurality of capacitors and the sampling node in parallel with respect to each other; and
a plurality of second switches, wherein each of the plurality of second switches is connected between a corresponding one of the plurality of capacitors and the second voltage in parallel with respect to each other,
wherein each of the plurality of first switches receives a corresponding bit of the tuning signal and each of the plurality of second switches receives a corresponding bit of an inverted version the tuning signal.

10. The ramp signal generator of claim 1, wherein the tuning circuit comprises:
a plurality of capacitors connected to the sampling node in parallel with respect to each other, wherein the plurality of capacitors have different capacitances with respect to each other;
a plurality of p-channel metal-oxide (PMOS) transistors, wherein each of the plurality of PMOS transistors is connected between a corresponding one of the plurality of capacitors and the first voltage in parallel with respect to each other; and
a plurality of n-channel metal-oxide (NMOS) transistors, wherein each of the plurality of NMOS transistors is connected between a corresponding one of the plurality of capacitors and the first output node in parallel with respect to each other,
wherein each gate of plurality of PMOS transistors and each gate of the plurality of NMOS transistors receive a corresponding bit of the tuning signal.

11. The ramp signal generator of claim 1, wherein the tuning circuit comprises:
a plurality of capacitors connected to the first output node in parallel with respect to each other, wherein the plurality of capacitors have different capacitances with respect to each other;
a plurality of n-channel metal-oxide (NMOS) transistors, wherein each of the plurality of NMOS transistors is connected between a corresponding one of the plurality of capacitors and the second voltage in parallel with respect to each other; and
a plurality of p-channel metal-oxide (PMOS) transistors, wherein each of the plurality of PMOS transistors is connected between a corresponding one of the plurality of capacitors and the sampling node in parallel with respect to each other,
wherein each gate of plurality of NMOS transistors and each gate of the plurality of PMOS transistors receive a corresponding bit of an inverted version of the tuning signal.

12. The ramp signal generator of claim 1, wherein the current to voltage converter further comprises a second load resistor connected between a second output node and the second voltage, wherein the second load resistor is configured to convert a second ramping current to a second ramp signal which is ramping during the ramping period, wherein the second ramping current is provided from the current cell circuit during the ramping period.

13. The ramp signal generator of claim 12, wherein:
the first ramp signal is down-ramping or up-ramping during the ramping period; and
the second ramp signal is ramping complementarily with the first ramp signal during the ramping period,
wherein the tuning circuit comprises:
a first tuner connected between the first output node and the sampling node, configured to adjust a degree of nonlinearity of the first ramp signal in response to the tuning signal; and a second tuner connected between the second output node and the sampling node, configured to adjust a degree of nonlinearity of a second ramp signal in response to the tuning signal.

14. The ramp signal generator of claim 13, wherein:
the first tuner includes a plurality of first capacitors connected between the first output node and the sampling node, in parallel with respect to each other, wherein the plurality of first capacitors have different capacitances with respect to each other; and
the second tuner includes a plurality of second capacitors connected between the second output node and the sampling node, in parallel with respect to each other, wherein the plurality of second capacitors have different capacitances with respect to each other.

15. The ramp signal generator of claim 14, wherein:
the plurality of first capacitors are configured to adjust the degree of nonlinearity of the first ramp signal by adjusting an amount by which the sampled bias voltage is coupled to the first ramp signal in response to the tuning signal; and
the plurality of second capacitors are configured to adjust the degree of nonlinearity of the second ramp signal by adjusting an amount by which the sampled bias voltage is coupled to the second ramp signal in response to the tuning signal.

16. The ramp signal generator of claim 12, wherein:
the first voltage is a power supply voltage and the second voltage is a ground voltage; or
the first voltage is a ground voltage and the second voltage is a power supply voltage.

17. An image sensor comprising:
a pixel configured to generate a reset signal and an image signal;
a comparator configured to compare the reset signal with a first ramp signal to generate a first comparison signal, and configured to compare the image signal with the first ramp signal to generate a second comparison signal;
a counter configured to count the first comparison signal based on a clock signal to generate a first counting value, and configured to count the second comparison signal based on the clock signal to generate a second counting value;
a ramp signal generator configured to generate at least the first ramp signal; and
a timing controller configured to control the pixel, the counter and the ramp signal generator,
wherein the ramp signal generator includes a tuning circuit connected between a first output node and a sampling node, the first ramp signal being provided at the first output node and a bias voltage being sampled at the sampling node, and
wherein the tuning circuit is configured to adjust a degree of nonlinearity of the first ramp signal in response to a tuning signal.

18. The image sensor of claim 17, wherein the ramp signal generator comprises:
a bias generation circuit connected between a first voltage and a second voltage, the bias generation circuit being configured to generate the bias voltage;
a transferring switch configured to transfer the bias voltage to the sampling node in response to a first switching control signal;
a sampling capacitor connected between the first voltage and the sampling node, the sampling capacitor configured to sample the bias voltage;
a current cell circuit configured to provide the first output node with a first ramping current during a ramping period, in response to a sampled bias voltage of the sampling node and a plurality of switching code pairs;
a current to voltage converter including a first load resistor connected between the first output node and the second voltage, wherein the first load resistor is configured to convert the first ramping current to the first ramp signal which is ramping during the ramping period; and
the tuning circuit connected between the first output node and the sampling node, the tuning circuit including at least one capacitor configured to couple the sampled bias voltage to the first ramp signal, wherein the tuning circuit is configured to adjust the degree of nonlinearity of the first ramp signal in response to the tuning signal.

19. The image sensor of claim 18, wherein the current to voltage converter further comprises a second load resistor connected between a second output node and the second voltage, wherein the second load resistor is configured to convert a second ramping current to a second ramp signal which is ramping during the ramping period, wherein the second ramping current is provided from the current cell circuit during the ramping period, and
wherein the tuning circuit comprises:
a first tuner connected between the first output node and the sampling node, the first tuner being configured to adjust the degree of nonlinearity of the first ramp signal in response to the tuning signal; and
a second tuner connected between the second output node and the sampling node, the second tuner being configured to adjust the degree of nonlinearity of the second ramp signal in response to the tuning signal.

20. A ramp signal generator of an image sensor, the ramp signal generator comprising:
a bias generation circuit connected between a first voltage and a second voltage, the bias generation circuit configured to generate a bias voltage;
a transferring switch configured to transfer the bias voltage to a sampling node in response to a first switching control signal;
a sampling capacitor connected between the first voltage and the sampling node, the sampling capacitor configured to sample the bias voltage;
a current cell configured to provide a first output node with a cell current, in response to a sampled bias voltage of the sampling node and a switching code pair;
a load resistor connected between the first output node and the second voltage, wherein the load resistor is configured to convert the cell current to a ramp signal; and
a tuning circuit connected between the first output node and the sampling node, the tuning circuit including at least one capacitor configured to couple the sampled bias voltage to the ramp signal, wherein the tuning circuit is configured to adjust a degree of nonlinearity of the ramp signal in response to a tuning signal.

* * * * *